US009878032B2

(12) United States Patent
Cox et al.

(10) Patent No.: US 9,878,032 B2
(45) Date of Patent: Jan. 30, 2018

(54) ATTENUATED INFLUENZA VACCINES AND USES THEREOF

(71) Applicant: UNIVERSITY OF ROCHESTER, Rochester, NY (US)

(72) Inventors: Andrew Cox, Rochester, NY (US); Stephen Dewhurst, Rochester, NY (US); John Treanor, Fairport, NY (US); Baek Kim, Atlanta, GA (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 0 days.

(21) Appl. No.: 14/905,320

(22) PCT Filed: Jul. 18, 2014

(86) PCT No.: PCT/US2014/047275
§ 371 (c)(1),
(2) Date: Jan. 15, 2016

(87) PCT Pub. No.: WO2015/010073
PCT Pub. Date: Jan. 22, 2015

(65) Prior Publication Data
US 2016/0136260 A1 May 19, 2016

Related U.S. Application Data

(60) Provisional application No. 61/856,442, filed on Jul. 19, 2013.

(51) Int. Cl.

| | |
|---|---|
| *A61K 39/145* | (2006.01) |
| *C12N 7/04* | (2006.01) |
| *A61K 39/12* | (2006.01) |
| *C12N 7/00* | (2006.01) |
| *C12N 9/12* | (2006.01) |
| *A61K 39/00* | (2006.01) |

(52) U.S. Cl.
CPC ........... *A61K 39/145* (2013.01); *A61K 39/12* (2013.01); *C12N 7/00* (2013.01); *C12N 7/04* (2013.01); *C12N 9/127* (2013.01); *A61K 2039/5254* (2013.01); *C12N 2760/00051* (2013.01); *C12N 2760/00062* (2013.01); *C12N 2760/16122* (2013.01); *C12N 2760/16134* (2013.01); *C12N 2760/16151* (2013.01); *C12N 2760/16171* (2013.01); *C12Y 207/07048* (2013.01)

(58) Field of Classification Search
None
See application file for complete search history.

(56) References Cited

U.S. PATENT DOCUMENTS 8,354,114 B2 1/2013 Lu et al.
2003/0099670 A1 5/2003 Hobom et al.
2004/0029251 A1 2/2004 Hoffman et al.
2008/0292658 A1* 11/2008 De Wit ................ C07K 14/005 424/206.1
2009/0074804 A1 3/2009 Lee et al.
2011/0150912 A1 6/2011 Perez
2013/0115242 A1 5/2013 Moules et al.

OTHER PUBLICATIONS

EP Application No. 14827095.2, extended European search report dated May 13, 2016, 11 pages.
Database UniProt [Online], XP002756977, Database accession No. Q9WLS3, Dec. 6, 2005.
Subbarao, et al., "Characterization of an Avian Influenza A (H5N1) Virus Isolated from a Child with a Fatal Respiratory Illness", Science, 279(5349):393-396, Jan. 16, 1998.
Database UniProt [Online], XP002756978, Database accession No. Q9ICX7, Oct. 1, 2000.
Lin, et al., "Avian-to-human transmission of H9N2 subtype influenza A viruses: Relationship between H9N2 and H5N1 human isolates", Proceedings of the National Academy of Sciences, 97(17):9654-9658, Aug. 15, 2000.
Ambrose et al., The efficacy of live attenuated and inactivated influenza vaccines in children as a function of time postvaccination, Pediatr. Infect. Dis. J., vol. 29, 2010, pp. 806-811.
Ambrose et al., The safety and efficacy of live attenuated influenza vaccine in young children with asthma or prior wheezing, Eur J. Clin MicrobiolInfect Dis., vol. 31, 2012, pp. 2549-2557.
Baker et al., Protection against lethal influenza with a viral mimic, J. Virol, vol. 87, 2013, pp. 8591-8605.
Belshe et al., Efficacy of live attenuated influenza vaccine in children 6 months to 17 years of age, Influneza Other Respir Viruses, vol. 4, 2010, pp. 141-145.
Belshe et al., Safety and efficacy of live attenuated influenza vaccine in children 2-7 years of age, Vaccine, vol. 26, Issue 4, 2008, pp. D10-D16.
Block et al., Shedding and immunogenicity of live attenuated influenza vaccine virus in subjects 5-49 years of age, Vaccine, vol. 26, 2008, pp. 4940-4946.
Bussey et al., PA residues in the 2009 H1 N1 pandemic influenza virus enhance avian influenza virus polymerase activity in mammalian cells, J. Viral., vol. 85, Issue 14, 2011, pp. 7020-7028.
Carter et al., Live attenuated influenza vaccine (FluMist(R); Fluenz): a review of its use in the prevention of seasonal influenza in children and adults, Drugs, vol. 71, 2011, pp. 1591-1622.
Cha et al., Genotypic stability of cold-adapted influenza virus vaccine in an efficacy clinical trial, J. Clin. Microbial. vol. 38, 2000, pp. 839-845.
Chan et al., The cold adapted and temperature sensitive influenza A/Ann Arbor/6/60 virus, the master donor virus for live attenuated influenza vaccines, has multiple defects in replication at the restrictive temperature, Virology, vol. 380, 2008, pp. 304-311.
Chen et al., Safety, immunogenicity, and efficacy of a cold-adapted A/Ann Arbor/6/60 (H2N2) vaccine in mice and ferrets, Virology, vol. 398, 2010, pp. 109-114.

(Continued)

*Primary Examiner* — Benjamin P Blumel
(74) *Attorney, Agent, or Firm* — Kilpatrick Townsend & Stockton LLP

(57) ABSTRACT

Provided herein are attenuated influenza viruses and methods of making attenuated influenza viruses.

18 Claims, 6 Drawing Sheets

(56) References Cited

OTHER PUBLICATIONS

Cox et al., Development of a Mouse-Adapted Live Attenuated Influenza Virus That Permits In Vivo Analysis of Enhancements to the Safety of Live Attenuated Influenza Virus Vaccine, Journal of Virology, vol. 89, Issue 6, Mar. 2015, pp. 3421-3426.
Cox et al., Identification of sequence changes in the cold-adapted, live attenuated influenza vaccine strain, A/Ann Arbor/6/60 (H2N2), Virology, vol. 167, 1988, pp. 554-567.
Da Costa et al., Temperature-sensitive mutants in the influenza A virus RNA polymerase: alterations in the PA linker reduce nuclear targeting of the PB1-PA dimer and hence result in viral attenuation, J. Virol. Doi: 10.1128/JVI.00589-15, Apr. 8, 2015, 47 pages.
Garaigorta et al., Genetic analysis of influenza virus NS1 gene: a temperature-sensitive mutant shows defective formation of virus particles, J. Virol, vol. 79, 2005, pp. 15246-15257.
Grimm et al., Replication fitness determines high virulence of influenza A virus in mice carrying functional Mx1 resistance gene, Proc Natl Acad Sci USA, vol. 104, 2007, pp. 6806-6811.
Grohskopf et al., Prevention and Control of Seasonal Influenza with Vaccines: Recommendations of the Advisory Committee on Immunization Practices (ACIP), Centers for Disease Control and Prevention. vol. 63(32), Aug. 15, 2014, pp. 691-697.
Jin et al., Imparting temperature sensitivity and attenuation in ferrets to A/Puerto Rico/8/34 influenza virus by transferring the genetic signature for temperature sensitivity from cold-adapted A/Ann Arbor/6/60, J. Virol, vol. 78, 2004, pp. 995-998.
Jin et al., Multiple amino acid residues confer temperature sensitivity to human influenza virus vaccine strains (FluMist) derived from cold-adapted A/Ann Arbor/6/60, Virology, vol. 306, 2003, pp. 18-24.
Kilbourne, Future influenza vaccines and the use of genetic recombinants, Bull World Health Organ, vol. 41, 1969, pp. 643-645.
Klein et al., Behavioral thermoregulation in mice inoculated with influenza virus, Physiol Behav, vol. 52, 1992, pp. 1133-1139.
Krammer et al., Assessment of influenza virus hemagglutinin stalk-based immunity in ferrets, J. Virol., vol. 88, 2014, pp. 3432-3442.
Krammer et al., Influenza virus hemagglutinin stalk-based antibodies and vaccines, Curr Opin Virol., vol. 3, 2013, pp. 521-530.
Maassab, Adaptation and growth characteristics of influenza virus at 25 degrees c, Nature, vol. 213, 1967, pp. 612-614.
Maassab et al., Biologic and immunologic characteristics of cold-adapted influenza virus, J. Immunol., vol. 102, 1969, pp. 728-732.
Margine et al., Hemagglutinin stalk-based universal vaccine constructs protect against group 2 influenza A viruses, J. Virol, vol. 87, 2013, pp. 10435-10446.
Martinez-Sobrido et al., Generation of recombinant influenza virus from plasmid DNA, J. Vis. Exp., vol. 42, e2057, 2010, 5 pages.
Meier-Ewert et al., Time course of synthesis and assembly of influenza virus proteins, Journal of virology, vol. 14, 1974, pp. 1083-1091.
Miller et al., Neutralizing antibodies against previously encountered influenza virus strains increase over time: a longitudinal analysis, Sci Transl. Med., vol. 5, 2013, pp. 198ra107.
Nogales et al., Influenza A virus attenuation by codon deoptimization of the NS gene for vaccine development, J. Virol, vol. 88, 2014, pp. 10524-1 0540.
Oster et al., Benefits and risks of live attenuated influenza vaccine in young children, Am. J. Manag. Care, vol. 16, 2010, pp. e325-e344.
Pflug et al., Structure of influenza A polymerase bound to the viral RNA promoter, Nature, vol. 000, 2014, pp. 1-16.
Reed et al., A simple method of estimating fifty per cent endpoints, Am. J. Hygiene, vol. 27, 1938, pp. 493-497.
Snyder et al., Four viral genes independently contribute to attenuation of live influenza A/Ann Arbor/6/60 (H2N2) cold-adapted reassortant virus vaccines, Journal of virology, vol. 62, 1988, pp. 488-495.
Suguitan et al., Live, attenuated influenza A H5N1 candidate vaccines provide broad cross-protection in mice and ferrets, PloS Med,vol. 3, e360, 2006, 15 pages.
Treanor et al., Evaluation of the genetic stability of the temperature-sensitive PB2 gene mutation of the influenza A/Ann Arbor/6/60 cold-adapted vaccine virus, Journal of virology, vol. 68, 1994, pp. 7684-7688.
Yang et al., Deliberate reduction of hemagglutinin and neuraminidase expression of influenza virus leads to an ultraprotective live vaccine in mice, Proc Natl Acad Sci U S.A., vol. 110, 2013, pp. 9481-9486.
Zhou et al., Engineering temperature sensitive live attenuated influenza vaccines from emerging viruses, Vaccine, vol. 30, 2012, pp. 3691-3702.
Zhou et al., Single-reaction genomic amplification accelerates sequencing and vaccine production for classical and Swine origin human influenza a viruses, J. Virol., vol. 19, 2009, pp. 10309-10313.
International Application No. PCT/US2014/047275, International Preliminary Report on Patentability dated Jan. 28, 2016, 8 pages.
International Application No. PCT/US2014/047275, International Search Report and Written Opinion dated Nov. 25, 2014, 14 pages.
U.S. Appl. No. 14/695,544, Non-Final Office Action dated Aug. 3, 2016, 13 pages.
Bowie, et al., Deciphering the Message in Protein Sequences: Tolerance to Amino Acid Substitutions, Science, 247:1306-1310.
Suzuki, et al., Amino Acid Substitutions in PB1 of Avian Influenza Viruses Influence Pathogenicity and Transmissibility in Chickens, Journal of Virology, 88(19): 11130-11139.
U.S. Appl. No. 14/695,544, Final Office Action dated Jan. 6, 2017, 7 pages.
U.S. Appl. No. 14/695,544, Advisory Action dated Jun. 1, 2017, 6 pages.
European Patent Application No. 14827095.2, Communication pursuant to Article 94(3) EPC dated May 31, 2017, 6 pages.

* cited by examiner

ATTENUATED INFLUENZA VACCINES AND USES THEREOF

This application claims the benefit of U.S. Provisional Application No. 61/856,442, filed Jul. 19, 2013, the disclosure of which is incorporated herein by reference in its entirety.

STATEMENT REGARDING FEDERALLY FUNDED RESEARCH

This invention was made with government support under grant number HHSN266200700008C, awarded by the National Institutes of Health. The government has certain rights in the invention.

BACKGROUND

Influenza is a serious public health issue marked by mild to serious illness and, in some cases, even death. Current live attenuated influenza vaccines (LAIV) are not sufficiently attenuated for administration to children under the age of 2, pregnant women, persons with compromised immunity, or persons at high risk for complications from influenza. However, these groups of people are at high risk for complications from influenza.

SUMMARY

Provided herein is a modified influenza A virus comprising a PB1 polymerase with one or more mutations in amino acids 310 to 325. Further provided is a recombinant nucleic acid encoding a PB1 polymerase of an influenza A virus, wherein the nucleic acid encodes a PB1 polymerase with one or more mutations in amino acids 310 to 325. Also provided are populations of cells comprising any of the influenza A viruses described herein or comprising any of the nucleic acids that encodes the PB1 polymerases described herein. The polymerase mutation results in a temperature sensitive virus, wherein the virus has reduced growth from about 37° C. to about 39° C. (i.e., at body temperature). This reduced growth potential is advantageous for improving the safety of the virus when used to induce an immune response.

Further provided is a method for eliciting an immune response against an influenza virus in a subject, comprising administering an effective dose of a modified influenza A virus described herein and a pharmaceutically acceptable carrier.

Also provided is a method for treating or preventing an influenza infection in a subject, comprising administering to a subject with an influenza infection or susceptible to an influenza infection an effective dose of a modified influenza A virus described herein, and a pharmaceutically acceptable carrier.

Also provided is a method of producing an influenza A virus described herein, comprising (a) transfecting a population of host cells with one or more vectors comprising i) nucleic acid sequences encoding the internal genome segments of an influenza A virus and; ii) a nucleic acid encoding a PB1 polymerase with one or more mutations in amino acids 310 to 325; (b) culturing the host cells; and (c) recovering the modified influenza A virus.

Further provided is a method for producing an influenza immunogen comprising (a) infecting a population of cells with any of the influenza A viruses described herein; (b) culturing the cells; (c) harvesting the virus from the culture of step (b); and (d) preparing an immunogen with the harvested virus.

DESCRIPTION

Figure 1:
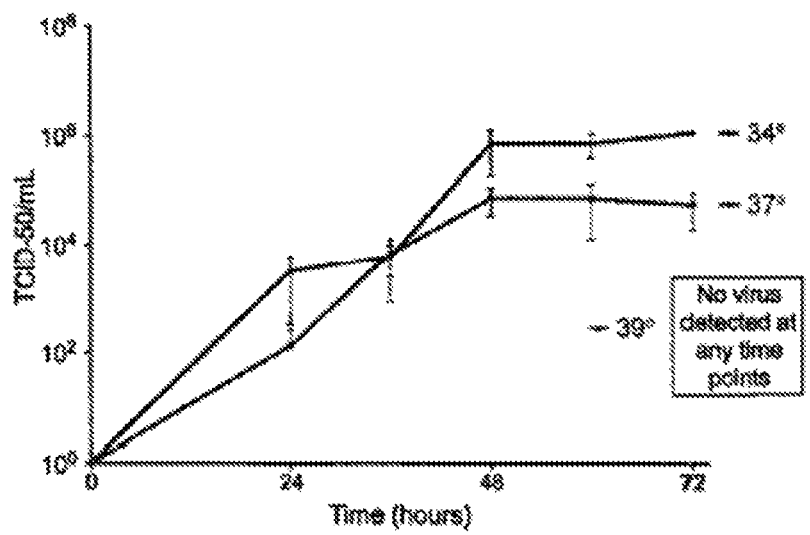
FIG. 1 shows the identification of a PB2 single gene replacement virus with temperature sensitivity at 37° C. MDCK cells were infected at a Multiplicity of Infection (MOI) of 0.01 for 1 h with a single gene replacement virus with PB2 from the cold passaged A/AnnArbor/6/60, and all other genes from a seasonal strain A/Korea/82. Cells were washed once with Dulbecco's phosphate-buffered saline (PBS) with magnesium and calcium (Invitrogen), and then cultured at 34°, 37° or 39° C. in DMEM containing 0.15% bovine serum albumin (BSA) and tosylsulfonylphenylalanyl chloromethyl ketone (TPCK)-trypsin at 1 µg/ml. At the indicated time points, 10% of the culture supernatant was harvested and replaced, and viral titers were determined through TCID-50 measurements.

Provided herein is a modified influenza A virus comprising a PB1 polymerase with one or more mutations in amino acids 310 to 325. Amino acids 310 to 325 of a PB1 polymerase are set forth herein as NENQNPRMFLAMITYI (SEQ ID NO: 1).

As used throughout, any influenza A virus can be modified to comprise a PB1 polymerase with one or more mutations in amino acids 310 to 325. For example, the influenza A virus can be selected from the group consisting of an H2N2 virus, an H3N2 virus, an H1N1 virus, an H9N2 virus and an H5N1 virus. Optionally, the influenza A virus can be selected from the group consisting of A/Ann Arbor/6/60, A/California/04/2009, A/Wisconsin/22/2011 and A/Quail/Hong Kong/G1/97. The influenza A virus can also be an avian influenza A virus. These include, but are not limited to, A/Chicken/Nanchang/3-120/01 H3N2, A/Hong Kong/485/1997(H5N1), A/Anhui/1/2013 (H7N9) and A/Shanghai/1/2013 (H7N9)

Resassortant influenza A viruses comprising one or more genomic segments from one or more influenza A viruses are also contemplated. More specifically, the virus includes genetic and/or polypeptide components derived from more than one parental viral strain or source. For example, a 7:1 reassortant includes 7 viral genomic segments (or gene segments) derived from a first parental virus and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus. Optionally, reassortant viruses are produced by introducing vectors including the six internal genes of a viral strain selected for its favorable properties regarding vaccine production, in combination with the genome segments encoding the surface antigens (HA and NA) of a selected, e.g., pathogenic strain. For example, the HA segment can be selected from an H1, H3 or B strain, as is routinely performed for vaccine production. Similarly, the HA segment can be selected from other pathogenic strains such as an H2 strain (e.g., H2N2), an H5 strain (e.g., H5N1), an H7 strain (e.g., H7N7) or an H9 strain (H9N2). In certain modified viruses, the internal gene segments are derived from the influenza A/Ann Arbor/6/60 strain.

As set forth herein, modifications include, but are not limited to, mutations in the amino acid sequence of a PB1 polymerase. Optionally, the one or more mutations in the PB1 polymerase are non-naturally occurring and are produced by human intervention (e.g., by mutagenesis of cloned DNA sequences), such as induced point mutation, deletion, insertion and substitution mutants. Amino acid sequence mutations typically fall into one or more of three classes: substitutional, insertional or deletional mutations. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than from about 2 to about 6 residues are deleted at any one site within the protein molecule. Amino acid substitutions are typically of single residues but can occur at a number of different locations at once, for example in one, two, three, four, five, six, seven or more amino acids of the polypeptide sequence set forth as SEQ ID NO: 1; insertions usually will be on the order of about from 1 to 10 amino acid residues; and deletions will range from about 1 to 10 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions can be made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Amino acid substitutions are not necessarily conservative as amino acid substitutions that change the side chain length, hydrophobicity or the polarity of a particular amino acid can also be made in order to alter the temperature sensitivity and/or increase the attenuation of virus.

In the PB1 polymerases described herein, one or more mutations in amino acids 310 to 325 can be selected from the group consisting of a leucine to glutamine substitution at position 319 (L319Q), an asparagine to valine substitution at position 310 (N310V), an asparagine to valine substitution at position 312 (N312V), a glutamine to leucine substitution at position 313 (Q313L), an asparagine to valine substitution at position 314 (N314V), a phenylalanine to tyrosine substitution at position 318 (F318Y), a leucine to glutamine substitution at position 3139 (L319Q), an alanine to threonine substitution at position 320 (A320T), an isoleucine to glutamine substitution at position 321 (I321Q), a threonine to alanine substitution at position 323 (T323A), a tyrosine to phenylalanine substitution at position 324 (Y324F) and an isoleucine to glutamine substitution at position 325 (I325Q).

It is understood that SEQ ID NO: 1 is an example of amino acids 310 to 325 of a PB1 polymerase. A sequence of amino acids 310 to 325 of any PB1 polymerase that is at least about 80%, 85%, 90%, or 95% identical to SEQ ID NO: 1 can also be modified as set forth herein.

Those of skill in the art readily understand how to determine the identity of two polypeptides or nucleic acids. For example, the identity can be calculated after aligning the two sequences so that the identity is at its highest level. Another way of calculating identity can be performed by published algorithms. Optimal alignment of sequences for comparison can be conducted using the algorithm of Smith and Waterman Adv. Appl. Math. 2: 482 (1981), by the alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.; the BLAST algorithm of Tatusova and Madden FEMS Microbiol. Lett. 174: 247-250 (1999) available from the National Center for Biotechnology Information, or by inspection.

The PB1 polymerases of any modified influenza A virus described herein can optionally comprise one or more mutations selected from the group consisting of a lysine to glutamic acid substitution at position 391 (K391E), a glutamic acid to glycine substitution at position 581 (E581G) and an alanine to threonine substitution at position 661 (A661T).

Any of the influenza A viruses described herein, including those with one or more mutations in a PB1 polymerase, as described above, can further comprise a PB2 polymerase comprising an asparagine to serine substitution at position 265 (N265S). Further, any of the influenza A viruses described can further comprise an influenza virus nucleoprotein (NP) comprising an aspartic acid to glycine substitution at position 35 (D35G).

Modifications, including the specific amino acid substitutions disclosed herein, are made by known methods. By way of example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

As used throughout, the PB1 polymerase can be any influenza A PB1 polymerase, including but not limited to, a A/Ann Arbor/6/60 H2N2 PB1 polymerase (GenBank Accession No. AY210012.1) (SEQ ID NO: 2), a A/California/04/2009 H1N1 PB1 polymerase (GenBank Accession No. GQ377049.1) (SEQ ID NO: 3), an H3N2 A/Wisconsin/22/2011 PB1 polymerase (GenBank Accession No. KC883051.1) (SEQ ID NO: 4) and a A/Quail/Hong Kong/G1/97 H9N2 and H5N1 PB1 polymerase (GenBank Accession No. AF156421.1) (SEQ ID NO: 5). Optionally, the nucleic acid sequence set forth under GenBank Accession No. AY210012.1 (SEQ ID NO: 6), also known as a nucleic acid sequence that encodes the Master Donor Virus (MDV) PB1 can comprise one or more mutations selected from the group consisting of A99G, A1171G, G1371T, A1742G, G1981A, and C1995T. Optionally, the PB1 nucleic acid sequence from A/Ann Arbor/6/60 comprises A99G, A1171G, G1371T, A1742G, G1981A, and C1995T.

As used throughout, the PB2 polymerase can be any influenza A PB2 polymerase, including but not limited to A/Ann Arbor/6/60 H2N2 PB2 polymerase (GenBank Accession No. AY209938) (SEQ ID NO: 7), A/Quail/Hong Kong/G1/97 H2N2 PB2 polymerase (GenBank Accession No. AF156435) (SEQ ID NO: 8), A/Shanghai/02/2013 H7N9 PB2 polymerase (Gen Bank Accession No. KF021594) (SEQ ID NO:9) or A/Chicken/Nanchang/3-120/2001 H3N2 PB2 polymerase (Gen Bank Accession No. AY180761) (SEQ ID NO: 10)

Recombinant nucleic acids encoding a PB1 polymerase of an influenza A virus, wherein the nucleic acid encodes a PB1 polymerase with one or more mutations in amino acids 310 to 325, are also provided. For example, a nucleic acid encoding a PB1 polymerase comprising a leucine to glutamine substitution at position 319 (L319Q) is provided herein. Further provided is a nucleic acid encoding a PB1 polymerase comprising a leucine to glutamine substitution at position 319 (L319Q) and one or mutations selected from the group consisting of a lysine to glutamic acid substitution at position 391 (K391E), a glutamic acid to glycine substitution at position 581 (E581G) and an alanine to threonine substitution at position 661 (A661T). Further provided are nucleic acids that encode both PB1 and PB2 polymerases with one or more mutations and compositions comprising nucleic acids that encode PB1 and PB2 polymerases with one or more mutations.

As used throughout, the term recombinant means that the material (e.g., a nucleic acid or protein) has been artificially or synthetically (non-naturally) altered by human intervention. It is understood that, when referring to a virus, e.g., an influenza A virus, the virus is recombinant when it is produced by the expression of a recombinant nucleic acid.

As used herein, nucleic acid refers to single or multiple stranded molecules which can be DNA or RNA, or any combination thereof, including modifications to those nucleic acids. For example, the nucleic acid can be a cDNA. The nucleic acid may represent a coding strand or its complement, or any combination thereof. The nucleic acid can be directly cloned into an appropriate vector, or if desired, can be modified to facilitate the subsequent cloning steps. Such modification steps are routine, an example of which is the addition of oligonucleotide linkers which contain restriction sites to the termini of the nucleic acid. General methods are set forth in in Sambrook et al. (2001) Molecular Cloning—A Laboratory Manual (3rd ed.) Vol. 1-3, Cold Spring Harbor Laboratory, Cold Spring Harbor Press, NY, (Sambrook).

The nucleic acids disclosed herein can be in any vector that can be used for the production of influenza virus in a host cell. The vector can direct the in vivo or in vitro synthesis of any of the polypeptides described herein, including, but not limited to PB1/and or PB2 polymerases. One or more of the vectors described herein can be part of a multi-vector system used to produce an influenza A virus. The vector is contemplated to have the necessary functional elements that direct and regulate transcription of the inserted nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene (See generally, Sambrook et al. (2001)). The vector, for example, can be a plasmid. The vectors can contain genes conferring hygromycin resistance, ampicillin resistance, gentamicin resistance, neomycin resistance or other genes or phenotypes suitable for use as selectable markers.

As used throughout, a host cell is a cell that contains one or more of the nucleic acids disclosed herein, including any of the nucleic acids in a vector, and supports the replication and/or expression of the nucleic acids, and optionally production of one or more encoded products including a polypeptide and/or a virus. Host cells can be prokaryotic cells, such as *E. coli*, or eukaryotic cells, such as yeast, insect, amphibian, avian or mammalian cells, including human cells. Examples of host cells include, but are not limited to, Vero (African green monkey kidney) cells, Per.C6 cells (human embryonic retinal cells), BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), CEK cells, primary human lung cells, bronchial epithelial cells, COS cells (e.g., COS 1, COST cells) and any other mammalian or avian cells that can be used to produce or propagate an influenza virus. The term host cell encompasses combinations or mixtures of cells including, but not limited to mixed cultures of different cell types or cell lines.

Any of the modified influenza A viruses described herein can be a live attenuated influenza A virus with reduced growth from about 37° C. to about 39° C., as compared to an influenza A virus comprising a PB1 polymerase lacking one or more mutations in amino acids 310 to 325. For example, the modified influenza A virus can have reduced growth at about 37° C., 38° C. or 39° C. or any temperature in between. Further, the modified influenza A virus can have reduced growth at about 37° C.-38° C. or at about 38° C.-39° C. Optionally, the modified influenza A virus grows at temperatures between about 32° C.-34° C. and has a reduction in growth at temperatures greater than about 34° C. In this way, the modified influenza A virus can grow, for example, in the upper respiratory tract where temperatures are about 32° C.-34° C., and stimulate an immune reaction, without producing symptoms in the lower respiratory tract where temperatures are about 37° C.-38° C. Optionally, the modified influenza A virus is attenuated at temperatures between about 32° C.-34° C. as well as between temperatures of about 37° C. to about 39° C. The degree of attenuation does not have to be the same at temperatures between about 32° C.-34° C. and at temperatures between temperatures of about 37° C. to about 39° C., as the reduction in growth at 32° C.-34° C. can be about the same or less than the reduction in growth at about 37° C. to about 39° C. Optionally, the virus exhibits at least about a 100-fold or greater reduction in titer at about 39° C. relative to titer at about 34° C.

As used throughout, ranges can be expressed herein as from about one particular value, and/or to about another particular value. When such a range is expressed, another aspect includes from the one particular value and/or to the other particular value. Similarly, when values are expressed as approximations, by use of the antecedent about it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as about that particular value in addition to the value itself. For example, if the value 10 is disclosed, then "about 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A reduction or a decrease in growth can be a decrease of about 10, 20, 30, 40, 50, 60, 70, 80, 90, 100% or any percentage in between as compared to an influenza A virus comprising a PB1 polymerase lacking one or more mutations in amino acids 310 to 325. Growth indicates viral quantity as indicated by titer, plaque size or morphology, particle density or other measures known to those of skill in the art. A reduction or decrease in growth can also be a reduction or decrease in replication of about 10, 20, 30, 40, 50, 60, 70, 80, 90, 100% or any percentage in between as compared to an influenza A virus comprising a PB1 polymerase lacking one or more mutations in amino acids 310 to 325.

Further provided is an immunogenic composition comprising any of the modified influenza A viruses disclosed herein and a pharmaceutically acceptable carrier to stimulate an immune response against one or more strains of influenza virus. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject. One of skill in the art would know how to select a carrier in order to minimize allergic and other undesirable effects, and to suit the particular route of administration. Optionally, the composition can further comprise an adjuvant.

Suitable carriers and their formulations are described in *Remington: The Science and Practice of Pharmacy, 21$^{st}$ Edition*, David B. Troy, ed., Lippicott Williams & Wilkins (2005). Examples of pharmaceutically-acceptable carriers include, but are not limited to, sterile water, saline, buffered solutions like Ringer's solution, glycerol solutions, ethanol, dextrose solutions, allantoic fluid from uninfected chicken eggs (i.e., normal allantoic fluid) or combinations thereof. The pH of the solution is generally about 5 to about 8 or from about 7 to 7.5. The preparation of such solutions insuring sterility, pH, isotonicity, and stability is effected according to protocols established in the art.

Other carriers include sustained release preparations such as semipermeable matrices of solid hydrophobic polymers containing the immunogenic composition. Matrices are in the form of shaped articles, e.g., films, liposomes, or microparticles. Certain carriers may be more preferable depending upon, for instance, the route of administration and concentration of composition being administered. Carriers are those suitable for administration of the compositions disclosed herein, to humans or other subjects.

Also provided is a method for eliciting an immune response against an influenza virus in a subject comprising administering an effective dose of any of the immunogenic compositions described herein. In the methods disclosed herein, the immune response can be an innate and/or an adaptive immune response. An immune response can be an antibody response against one or more strains of influenza and/or a T cell mediated response.

As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with or at risk of developing an influenza infection. The term patient or subject includes human and veterinary subjects.

According to the methods taught herein, the subject is administered an effective amount of the agent, e.g., an immunogenic composition comprising a modified influenza A virus. The terms effective amount and effective dosage are used interchangeably. The term effective amount is defined as any amount necessary to produce a desired physiologic response (i.e., an immune response). Effective amounts and schedules for administering the agent may be determined empirically, and making such determinations is within the skill in the art. The dosage ranges for administration are those large enough to produce the desired effect (e.g., eliciting an immune response to the antigen of interest, i.e. influenza A). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and the agent can be administered in one or more dose administrations daily, for one or several days, including a prime and boost paradigm.

The compositions are administered via any of several routes of administration, including, but not limited to, orally, parenterally, intravenously, intramuscularly, subcutaneously, transdermally, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol. A form of administration that results in an immune response can be used by one of skill in the art to optimize the response.

In any of the methods described herein, the immunogenic compositions can be used alone or in combination with one or more therapeutic agents such as, for example, antiviral compounds for the treatment of influenza. These include, but are not limited to, amantadine, rimantadine, ribavirin, zanamavir (Relenza®) and oseltamavir (Tamiflu®).

Further provided is a method of treating or preventing an influenza infection in a subject, comprising administering to a subject with an influenza infection or susceptible to an influenza infection an effective dose of any of the immunogenic compositions described herein.

For purposes of vaccines, the subject may be healthy and without higher risk than the general public. A subject at risk of developing an influenza infection, however, can be predisposed to contracting an infection (e.g., persons over 65, persons with asthma or other chronic respiratory disease, young children, pregnant women, persons with a hereditary predisposition, persons with a compromised immune system or by being in an environment that facilitates the passage of an influenza infection). A subject currently with an infection has one or more than one symptom of the infection. These symptoms include, but are not limited, fever, sore throat, cough, muscle aches, headache, fatigue, vomiting and diarrhea. The subject currently with an influenza infection may have been diagnosed with an influenza infection.

The methods and compositions as described herein are useful for both prophylactic and therapeutic treatment. For prophylactic use, a therapeutically effective amount of the compositions described herein are administered to a subject prior to onset (e.g., before obvious signs of infection) or during early onset (e.g., upon initial signs and symptoms of infection). Prophylactic administration can occur for several days to years prior to the manifestation of symptoms of the infection. Prophylactic administration can be used, for example, in the preventative treatment of subjects diagnosed with a predisposition to influenza infection. Therapeutic treatment involves administering to a subject a therapeutically effective amount of the agents described herein after diagnosis or development of infection.

As used herein the terms treatment, treat, or treating refers to a method of reducing one or more of the effects of the infection or one or more symptoms of the infection by eliciting an immune response in the subject. Thus in the disclosed method, treatment can refer to a 10%, 20%, 30%, 40%, 50%, 60%, 70%, 80%, 90%, or 100% reduction in the severity of an established infection or a symptom of the infection. For example, a method for treating an infection is considered to be a treatment if there is a 10% reduction in one or more symptoms of the infection in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection or disease or symptoms of the infection or disease.

As used herein, the terms prevent, preventing, and prevention of an infection, refers to an action, for example, administration of a therapeutic agent (e.g., a composition disclosed herein), that occurs before or at about the same time a subject begins to show one or more symptoms of the infection, which inhibits or delays onset or exacerbation or delays recurrence of one or more symptoms of the infection. As used herein, references to decreasing, reducing, or inhibiting include a change of 10%, 20%, 30%, 40%, 50%, 60%, 70%, 80%, 90% or greater as compared to a control level. For example, the disclosed methods are considered to be a prevention if there is about a 10% reduction in onset, exacerbation or recurrence of infection, or symptoms of infection in a subject exposed to an infection when compared to control subjects exposed to an infection that did not receive a composition for decreasing infection. Thus, the reduction in onset, exacerbation or recurrence of infection can be about a 10, 20, 30, 40, 50, 60, 70, 80, 90, 100%, or any amount of reduction in between as compared to control subjects. For example, and not to be limiting, if about 10%> of the subjects in a population do not become infected as compared to subjects that did not receive preventive treatment, this is considered prevention.

Further provided is a method of producing the influenza A viruses disclosed herein comprising (a) transfecting a population of host cells with one or more vectors comprising (i) nucleic acid sequences encoding the internal genome segments of an influenza A virus and; (ii) a nucleic acid encoding a PB1 polymerase with one or more mutations in amino acids 310 to 325; (b) culturing the host cells; and c) recovering the modified influenza A virus. Methods for producing influenza virus are known to those of skill in the art. In the production methods described herein, plasmids incorporating the internal genes of an influenza master virus strain, (i.e., PB1, PB2, PA, NP, N13, M1, BM2, NS1 and NS2) are transfected into suitable host cells in combination with hemagglutinin and neuraminidase segments. See, for example, U.S. Pat. No. 8,354,114, incorporated herein by reference. Optionally, the hemagglutinin and neuraminidase segments can be from a strain predicted to cause significant local or global influenza infection. Typically, the master strain is selected on the basis of desirable properties relevant to vaccine administration. For example, for vaccine production, e.g., for production of a live attenuated vaccine, the master donor virus strain can be selected for an attenuated phenotype, cold adaptation and/or temperature sensitivity. For example, Influenza A strain ca A/Ann Arbor/6/60 can be the master donor virus (see, for example, Chan et al., *Virology* 380: 304-311 (2008). Following replication of the reassortant virus in cell culture at appropriate temperatures for efficient recovery, for example, at temperatures equal to or less than about 35° C., such as from about 32° C. to 35° C., from about 32° C. to about 34° C., or from about 32° C. to about 33° C., the reassortant virus is recovered. Optionally, the recovered virus can be inactivated using a denaturing agent such as formaldehyde or β-propiolactone. Optionally, in the production methods provided herein, the viruses can be further amplified in chicken eggs.

Further provided is a method for producing an influenza vaccine comprising (a) infecting a population of cells with any of the viruses described herein; (b) culturing the cells; (c) harvesting the virus from the culture of step (b); and (d) preparing a vaccine with the harvested virus.

Once the virus is harvested from a cell culture, the virus can be formulated and administered as a composition, according to known methods, as an immunogenic composition to induce an immune response in an animal, e.g., a mammal. Optionally, the immunogenic composition can be formulated as an inactivated vaccine. Methods are well-known in the art for determining whether such inactivated vaccines have maintained similar antigenicity to that of the clinical isolate or a high growth strain derived therefrom. As set forth above, an immunogenic composition can be administered via all the routes conventionally used or recommended for an immunocgenic composition. The immunogenic composition can be formulated as an injectable or sprayable liquid, or as a formulation which has been freeze-dried or dried by atomization or air-dried, etc. The immunogenic composition can also be formulated for administration via syringe or by means of a needle-free injector for intramuscular, subcutaneous or intradermal injection. The immunogenic composition can also be administered by means of a nebulizer capable of delivering a dry powder or a liquid or aerosolized spray to the mucous membranes.

A complete immunogenic composition can be concentrated by ultrafiltration and then purified by zonal centrifugation or by chromatography. Optionally, it can be inactivated before or after purification using formalin or β-propiolactone, for example.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

Examples

The current live attenuated influenza vaccine (LAW) is recommended as the primary vaccination strategy for healthy subjects aged 2 to 49 years, because of its greater efficacy and ease-of-use than the traditional inactivated influenza vaccine in this age group. However, the current LAW is not recommended for pregnant women, children under 2, persons with a compromised immune system, (for example, persons with HIV/AIDS), or persons at high risk for complications from influenza.

The current LAIV vaccine was originally derived through cold adaptation, and subsequent work determined that the attenuating gene segments correspond to the viral polymerase (PB1, PB2, PA) and nucleoprotein (NP). Introduction of the attenuating PB2 segment into the genetic background of a seasonal influenza virus background resulted in temperature sensitivity and attenuation, which could be overcome by serial passage of virus at elevated temperatures.

These phenotypic revertant viruses were analyzed with the goal of understanding the molecular mechanism underlying the attenuation of LAIV. Methods for isolating and characterizing mutant viruses, including characterization of temperature-sensitivity are described in Treanor et al. ("Evaluation of the genetic stability of temperature-sensitive PB2 gene mutation of the influenza A/Ann Arbor/6/60 cold-adapted vaccine virus," *J. Virol.* 68(12): 7684-8 (1994)), which is hereby incorporated in its entirety by this reference.

A mutation that results in a leucine to glutamine substitution at position 319 of PB1 was made using the methods described herein. The polymerase activity of the mutant was assayed using a minigenome assay described in Bussey et al. ("PA residues in the 2009 H1N1 pandemic influenza virus enhance avian influenza virus polymerase activity in mammalian cells," *J. Virol.* 85(14): 7020-8 (2011)), which is hereby incorporated in its entirety by this reference. It was found that a mutation in the PB1 gene (at residue 319) was sufficient to reverse the temperature sensitive phenotype of the viral RNA polymerase, conferred by the LAW PB2 gene segment. This was unexpected, since previous studies have identified such reversion mutations only in the PA gene. Follow up studies revealed that the 319 mutation was also sufficient to reverse the temperature-sensitivity of the RNA polymerase from two avian strains in the H5N1 and H9N2 lineage, thus showing that the PB1 319 residue has broad relevance in determining the temperature sensitivity of the virus polymerase. Collectively, these studies revealed a novel molecular determinant of the temperature sensitivity and attenuation of the influenza A virus RNA polymerase.

The following study was performed by constructing and characterizing mutant viruses as set forth in Treanor et al. Viruses were characterized for temperature sensitivity in the following manner: confluent 6 well plates of MDCK cells were infected at an MOI of 0.01 with the is single gene replacement virus and incubated at 34, 37 and 39° C. for 72 hours. Every 12 hours a sample of the culture supernatant was harvested and replaced with fresh media. These samples were clarified by centrifugation and stored at −80° C. The samples were then analyzed for viral titer through TCID-50 analysis, as described in Bussey et al. The virus used in this analysis possessed the PB2 segment of cold adapted temperature sensitive and attenuated A/Ann Arbor/6/60 (Genbank ID: AY209938.1) in the background of A/Korea/1982 (see Treanor et al.).

As set forth above, the PB2 segment of a seasonal human influenza A virus strain (A/Korea/82 H3N2) was replaced with the PB2 segment from the cold passaged isolate of A/AnnArbor/6/60. The resulting single gene replacement virus is temperature sensitive (ts) for growth at elevated temperatures. This virus stock was subjected to serial passage at increasing temperatures, in order to identify phenotypically revertant single gene replacement viruses. The ts PB2 single gene replacement virus was subjected to plaque purification and individual plaques were analyzed for their temperature dependent growth properties. The plaque purified viruses were expected to have growth at 34° C. and 37° C. but not at 39° C. (see FIG. 1). Surprisingly, a virus that had reduced growth at 37° C. as well as at 39° C. was purified.

Figure 2:
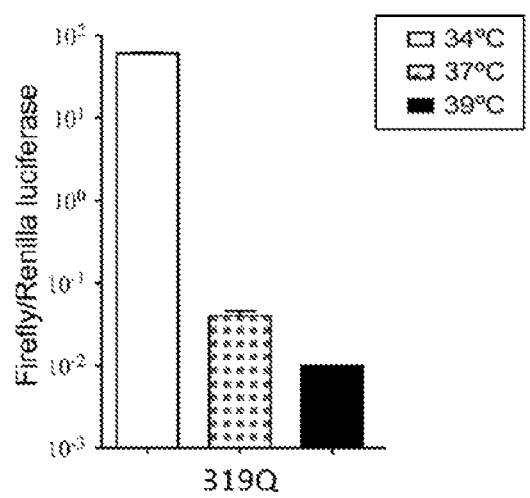
FIG. 2 shows that the PB1 319Q mutation significantly reduces functional activity of the human influenza A virus RNA polymerase at 37° C. The polymerase activity of the indicated polymerases was characterized in human HEK-293FT cells by quantifying luciferase activity in the clarified cell lysates of cells transfected with PB1-, PB2-, PA-, and NP-protein expression plasmids along with a reporter plasmid expressing an influenza virus-like RNA construct for firefly luciferase. The cells were incubated at the indicated temperatures. All assays utilized the same NP plasmid. Depicted is the ratio of firefly to renilla luminescence. Data are averaged over a minimum of three independent experiments. Error bars represent one standard error of the mean. All plasmids used in this mini-genome assay were identical, except for the PB1 plasmid, which encoded a Q at residue 319 (as indicated). These plasmids were created from viral stocks through cloning the consensus sequence from viral growth curves into the mammalian pCAGGS expression vector.

All components of the viral polymerase were cloned into a mammalian expression vector from the viral RNA and then analyzed. Surprisingly this system revealed a significant decrease in polymerase activity at 37° C. A number of residues were found to be unique as compared to conserved influenza sequences and their importance was examined through mutation to the conserved residue by site directed mutagenesis. A residue of interest resided in PB1, at amino acid 319, and was the substitution of a polar glutamine for a nonpolar leucine. The PB1 L319Q mutation dramatically reduces functional activity of human influenza A virus RNA polymerase at 37° C. (see FIG. 2).

Figure 3:
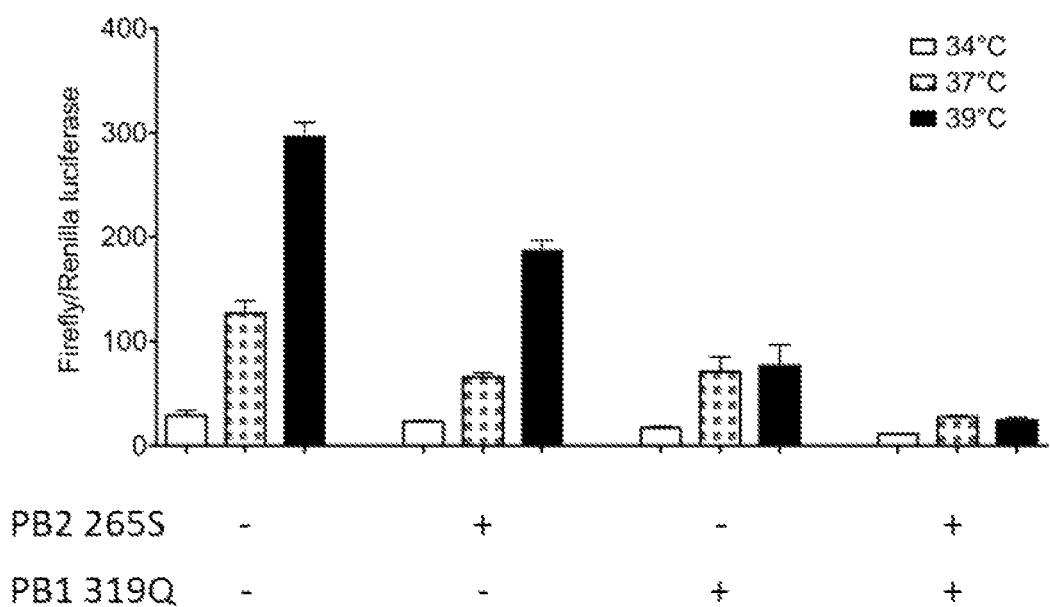
FIG. 3 shows that the PB1 L319Q mutation reduces functional activity of an avian influenza A virus RNA polymerase at 37° C. The polymerase activity of each viral polymerase was characterized in human HEK-293FT cells by quantifying luciferase activity in the clarified cell lysates of cells transfected with PB1-, PB2-, PA-, and NP-protein expression plasmids along with a reporter plasmid expressing an influenza virus-like RNA construct for firefly luciferase. The cells were incubated at the indicated temperatures. Depicted is the ratio of firefly to renilla luminescence. Data are averaged over a minimum of 3 independent experiments. Error bars represent one standard error of the mean. In this experiment, all polymerase gene segments were derived from avian influenza viruses. The PA and PB2 segments were derived from A/California/04/09 H1N1, and the PB1 and NP segments were derived from A/Chicken/Nanchang/3 H3N2. Plasmids differed only at the indicated residues: (1) PB2 encoding either 265S or 265N [wild-type]; (2) encoding either 319Q or 319L [wild-type].
Figure 4:
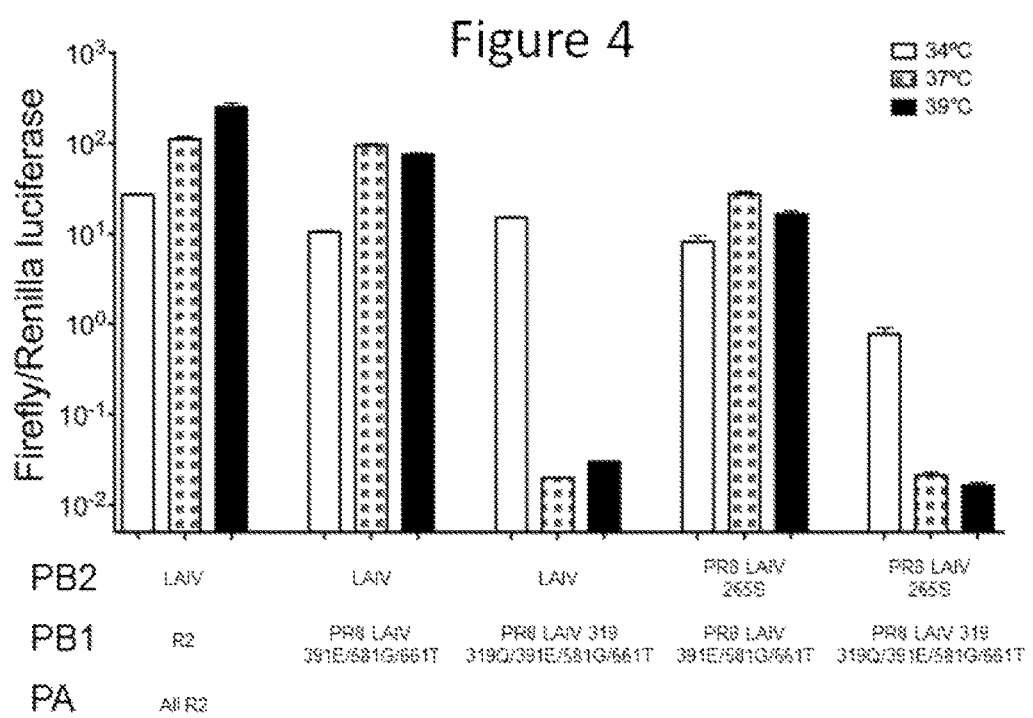
FIG. 4 shows the effects of a 319Q mutation in PB1, in combination with three mutations present in LAIV PB1.

The impact of this mutation on other influenza A viruses (IAV) was then examined. In these experiments an avian IAV polymerase complex, the polymerase complex from the low-pathogenicity virus, A/Chicken/Nanchang/3-120/01 H3N2, was used. Introduction of the L319Q mutation in PB1 into this polymerase also significantly reduced the functional activity of this avian influenza A virus RNA polymerase at 37° C. (FIG. 3). It was also found that a PB1 with a L319Q mutation synergizes with three mutations (K391E, E581G and A661T) found in the LAIV (FIG. 4). The polymerase activity was assayed using the minigenome assay described in Bussey et al.

Figure 5:
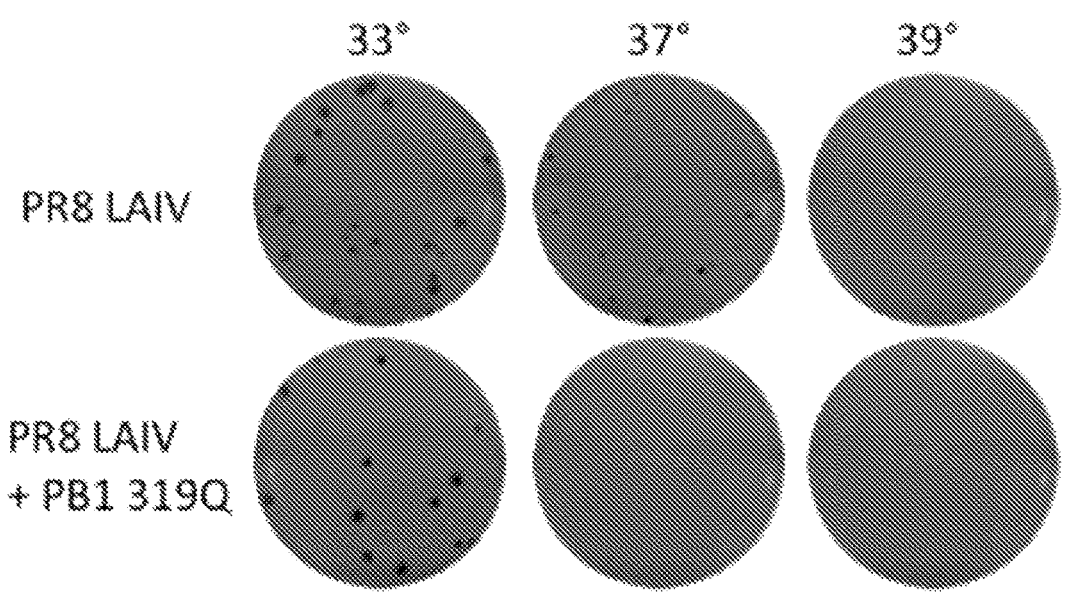
FIG. 5 shows the effects of a 319Q mutation in PB1, in combination with four mutations present in LAIV PB1.

Additional experiments were conducted to further characterize the temperature sensitivity of a modified vaccine strain virus. Viruses were created through site directed mutagenesis of the PR8 bidirectional plasmids described in Martinez-Sobrido et al. ("Generation of Recombinant Influenza Virus from Plasmid DNA," J. Vis. Exp. 42: 2057 (2010)). PR8 live attenuated influenza virus (LAIV) possesses 4 amino acid mutations. These mutations are N265S in PB2, K391E in PB1, E581G in PB1 and A661T in PB1. PR8 LAIV+PB1 319Q possesses the mutation PB1 L319Q in addition to the 4 mutations present in PR8 LAIV. All plasmids were sequenced to confirm successful site directed mutagenesis and all rescued viruses were sequenced to confirm retention of only the desired mutations. Both viruses were assayed for temperature-sensitive growth via plaque assay, as described in Bussey et al. When the four mutations of LAIV (N265S in PB2, K391E in PB1, E581G in PB1 and A661T in PB1) were added to PR8 no virus was detected by plaque assay at 39° C. However, when PB1 319Q was added in addition to the four mutations of LAIV, no virus growth occurred at 37° C. as well (FIG. 5).

Figure 6:
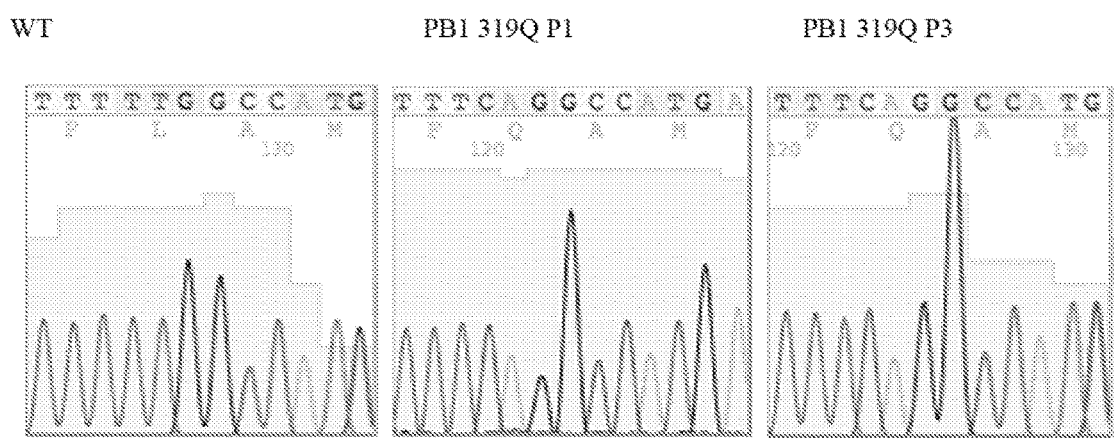
FIG. 6 shows the stability of the mutation at position 319 of PB1.

Experiments were also conducted to characterize the stability of the L319Q mutation. The stability of a glutamine at residue 319Q of PB1 was analyzed by inserting this mutation singly in the background of a wild type virus to determine whether this mutation is stable. These viruses were constructed via site-directed mutagenesis of the PR8 bidirectional plasmids described in Martinez-Sobrido et al. PB1 319Q possesses glutamine instead of the wildtype leucine at residue 319 of PB1. All plasmids were sequenced to confirm successful site-directed mutagenesis and all rescued viruses were sequenced to confirm retention of only the desired mutations. The viruses were then passaged an additional three times at 30° C., 33° C., 37° C. and 39° C. The PB1 gene was then sequenced in its entirety as described in Zhou et al ("Single-reaction genomic amplification accelerates sequencing and vaccine production for classical and Swine origin human influenza a viruses," J. Virol. 19: 10309-13 (2009)), which is incorporated herein in its entirety by this reference. After 1 passage the virus showed uniform stability. After 2 subsequent passages at 30° C., 33° C., 37° C. and 39° C., all viruses retained glutamine at this position. This shows that this mutation is stable at various temperatures in influenza A viruses (FIG. 6).

Thus, a novel and unexpected mutation in PB1(L319Q), that increases the temperature sensitivity of influenza A viruses was identified. Therefore, this and other mutations can be used to make live attenuated influenza viruses. These mutations can also be used to further attenuate existing live attenuated influenza viruses (LAIV), thereby increasing their safety, and allowing for its use in populations in which the vaccine is presently contraindicated.

SEQUENCES

SEQ ID NO: 1

NENQNPRMFLAMITYI

SEQ ID NO: 2

MDVNPTLLFLKVPAQNAISTTFPYTGDPPYSHGTGTGYTMDTVNRTHQYSEKGKWT

TNTETGAHQLNPIDGPLPEDNEPSGYAQTDCVLEAMAFLEESHPGIFENSCLETMEVI

QQTRVDKLTQGRQTYDWTLNRNQPAATALANTIEVFRSNGLTANESGRLIDFLKDVI

ESMDKEEMEITTHFQRKRRVRDNMTKKMVTQRTIGKKKQRLNKRSYLIRALTLNTM

TKDAERGKLKRRAIATPGMQIRGFVYFVETLARSICEKLEQSGLPVGGNEKKAKLAN

VVRKMMTNSQDTELSFTITGDNTKWNENQNPRMFLAMITYITRNQPEWFRNVLSIAP

IMFSNKMARLGKGYMFKSKSMKLRTQIPAEMLASIDLKYFNESTRKKIEKIRPLLIDG

```
TVSLSPGMMMGMFNMLSTVLGVSILNLGQKKYTKTTYWWDGLQSSDDFALIVNAP
NHEGIQAGVDRFYRTCKLVGINMSKKKSYINRTGTFEFTSFFYRYGFVANFSMELPSF
GVSGINESADMSIGVTVIKNNMINNDLGPATAQLALQLFIKDYRYTYRCHRGDT
QIQTRRSFELKKLWEQTRSKAGLLVSDGGPNLYNIRNLHIPEVCLKWELMDEDYQGR
LCNPLNPFVSHKEIESVNNAVVMPAHGPAKSMEYDAVATTHSWIPKRNRSILNTSQR
GILEDEQMYQKCCNLFEKFFPSSSYRRPVGISSMVEAMVSRARIDARIDFESGRIKKEE
FAEIMKICSTIEELRRQK
```

SEQ ID NO: 3
```
MDVNPTLLFLKIPAQNAISTTFPYTGDPPYSHGTGTGYTMDTVN
RTHQYSEKGKWTTNTETGAPQLNPIDGPLPEDNEPSGYAQTDCVLEAMAFLEESHPG
IFENSCLETMEVVQQTRVDKLTQGRQTYDWTLNRNQPAATALANTIEVFRSNGLTA
NESGRLIDFLKDVMESMNKEEIEITTHFQRKRRVRDNMTKKMVTQRTIGKKKQRLN
KRGYLIRALTLNTMTKDAERGKLKRRAIATPGMQIRGFVYFVETLARSICEKLEQSGL
PVGGN
EKKAKLANVVRKMMTNSQDTEISFTITGDNTKWNENQNPRMFLAMITYITRNQPEW
FRNILSMAPIMFSNKMARLGKGYMFESKRMKIRTQIPAEMLASIDLKYFNESTKKKIE
KIRPLLIDGTASLSPGMMMGMFNMLSTVLGVSILNLGQKKYTKTIYWWDGLQSSDD
FALIVNAPNHEGIQAGVDRFYRTCKLVGINMSKKKSYINKTGTFEFTSFFYRYGFVAN
FSMELPSFGVSGVNESADMSIGVTVIKNNMINNDLGPATAQMALQLFIKDYRYTYRC
HRGDTQIQTRRSFELKKLWDQTQSKVGLLVSDGGPNLYNIRNLHIPEVCLKWELMD
DDYRGRLCNPLNPFVSHKEIDSVNNAVVMPAHGPAKSMEYDAVATTHSWIPKRNRS
ILNTSQRGILEDEQMYQKCCNLFEKFFPSSSYRRPVGISSMVEAMVSRARIDARVDFE
SGRIKKEEFSEIMKICSTIEELRRQK
```

SEQ ID NO: 4
```
MDVNPTLLFLKVPAQNAISTTFPYTGDPPYSHGTGTGYTMDTVN
RTHQYSERGKWTTNTETGAPQLNPIDGPLPEDNEPSGYAQTDCVLEAMAFLEESHPG
IFENSCLETMEAVQQTRVDKLTQGRQTYDWTLNRNQPAATALANTIEVFRSNGLTA
NESGRLIDFLKDVMESMDKEEMEITTHFQRKRRVRDNMTKKMVTQRTIGKKKQRV
NKRGYLIRALTLNTMTKDAERGKLKRRAIATPGMQIRGFVYFVETLARSICEKLEQS
GLPVGGNEKKAKLANVVRKMMTNSQDTELSFTITGDNTKWNENQNPRMFLAMITYI
TKNQPEWFRNILSIAPIMFSNKMARLGKGYMFESKKMKLRTQIPAEMLASIDLKYFN
ESTRKKIEKIRPLLIDGTASLSPGMMMGMFNMLSTVLGVSILNLGQKKYTKTTYWW
DGLQSSDDFALIVNAPNHEGIQAGVDRFYRTCKLVGINMSKKKSYINKTGTFEFTSFF
YRYGFVANFSME
LPSFGVSGINESADMSIGVTVIKNNMINNDLGPATAQMALQLFIKDYRYTYRCHRGD
TQIQTRRSFEIKKLWDQTQSRAGLLVSDGGPNLYNIRNLHIPEVCLKWELMDENYRG
RLCNPLNPFVSHKEIESVNNAVVMPAHGPAKSMEYDAVATTHSWIPKRNRSILNTSQ
RGILEDEQMYQKCCNLFEKFFPSSSYRRPIGISSMVEAMVSRARIDARIDFESGRIKKE
EF
SEIMRICSTIEELRRQK
```

SEQ ID NO: 5

MDVNPTLLFLKVPAQNAISTTFPYTGDPPYSHGTGTGYTMDTVN

RTHQYSEKGRWTTNTETGAPQLNPIDGPLPEDNEPSGYAQTDCVLEAMAFLEESHPG

LFENSCLETMEVVQQTRVDKLTQGRQTYDWTLNRNQPAATALANTIEVFRSNGLTA

NESGRLIDFLKDVMESMDKEEMEITTHFQRKRRVRDNMTKKMVTQRTIGKKKQKLT

KKSYLIRALTLNTMTKDAERGKLKRRAIATPGMQIRGFVHFVEALARSICEKLEQSGL

PVGGN

EKKAKLANVVRKMMTNSQDTELSFTVTGDNTKWNENQNPRIFLAMITYITRNQPEW

FRNVLSIAPIMFSNKMARLGKGYMFESKSMKLRTQIPAEMLANIDLKYFNESTRKKIE

KIRPLLIEGTASLSPGMMMGMFNMLSTVLGVSILNLGQKRYTKTTYWWDGLQSSDD

FALIVNAPNHEGIQAGVDRFYRTCKLVGINMSKKKSYINRTGTFEFTSFFYRYGFVAN

FSME

LPSFGVSGINESADMSIGVTVIKNNMINNDLGPATAQMALQLFIKDYRYTYRCHRGD

TQIQTRRSFELKKLWEQTRSKAGLLVSDGGPNLYNIRNLHIPEVGLKWELMDEDYQG

RLCNPLNPFVSHKEVESVNNAVVMPAHGPAKSMEYDAVATTHSWIPKRNRSILNTS

QRGILEDEQMYQKCCTLFEKFFPSSSYRRPVGISSMMEAMVSRARIDARIDFESGRIK

KEEFAEIL

SEQ ID NO: 6

```
   1 atggatgtca atccgacctt acttttcttg aaagttccag cgcaaaatgc cataagtact
  61 acattccctt atactggaga tcctccatac agccatggaa caggaacagg atacaccatg
 121 gacacagtca acagaacaca tcaatattca gaaaggggga gtggacaac aaacacggaa
 181 actggagcgc accaacttaa cccaattgat ggaccactac ctgaggacaa tgaaccaagt
 241 ggatatgcac aaacagactg cgtcctggaa gcaatggctt ccttgaaga atcccaccca
 301 ggaatctttg aaaactcgtg tcttgaaacg atggaagtta ttcaacaaac aagagtggac
 361 aaactgaccc aaggtcgtca gacctatgat tggacattga acagaaatca gccggctgca
 421 actgcgctag ccaacactat agaggtcttc agatcgaatg gcctgacagc taatgaatcg
 481 ggaaggctaa tagatttcct caaggatgtg atagaatcaa tggataaaga ggagatggaa
 541 atcacaacac acttccaaag aaaaagaaga gtaagagaca catgaccaa gaaaatggtc
 601 acacaacgaa caataggaaa gaagaagcaa agattgaaca agagaagcta tctaataaga
 661 gcactgacat tgaacacaat gactaaagat gcagagagag gtaaattaaa gagaagagca
 721 attgcaacac ccggtatgca gatcagaggg ttcgtgtact tgtcgaaac actagcgaga
 781 agtatttgtg agaagcttga acagtctggg cttccggttg gaggtaatga aaagaaggct
 841 aaactggcaa atgttgtgcg aaaaatgatg actaattcac aagacacaga gctctctttc
 901 acaattactg gagacaatac caatggaat gagaatcaaa atcctcggat gttcctggcg
 961 atgataacat acatcacaag aaatcaacct gaatggttta gaacgtcct gagcatcgca
1021 cctataatgt tctcaaataa aatggcaaga ctagggaaag gatacatgtt caaaagcaag
1081 agcatgaagc tccgaacaca ataccagca gaaatgctag caagtattga cctgaaatac
1141 tttaatgaat caacaagaaa gaaaatcgag aaaataaggc ctctcctaat agatggcaca
1201 gtctcattga gtcctggaat gatgatgggc atgttcaaca tgctaagtac agtcttagga
1261 gtctcaatcc tgaatcttgg acaaaagaag tacaccaaaa caacatactg gtgggacgga
1321 ctccaatcct ctgatgactt cgccctcata gtgaatgcac caaatcatga gggaatacaa
```

-continued

```
1381 gcaggggtgg atagattcta cagaacctgc aagctagtcg gaatcaatat gagcaaaaag
1441 aagtcctaca taaataggac agggacattt gaattcacaa gcttttttcta tcgctatgga
1501 tttgtagcca attttagcat ggagctgccc agctttggag tgtctggaat taatgaatcg
1561 gctgatatga gcattggggt aacagtgata agaacaaca tgataaacaa tgaccttggg
1621 ccagcaacag cccaactggc tcttcaacta ttcatcaaag actacagata tacgtaccgg
1681 tgccacagag gagacacaca aattcagaca aggagatcat tcgagctaaa gaagctgtgg
1741 gagcaaaccc gctcaaaggc aggacttttg gtttcggatg gaggaccaaa cttatacaat
1801 atccggaatc tccacattcc agaagtctgc ttgaagtggg agctaatgga tgaagactat
1861 caggggaggc tttgtaatcc cctgaatcca tttgtcagtc ataaggagat tgagtctgta
1921 aacaatgctg tggtaatgcc agctcacggt ccagccaaga gcatggaata tgatgctgtt
1981 gctactacac actcctggat ccctaagagg aaccgctcca ttctcaacac aagccaaagg
2041 ggaattcttg aagatgaaca gatgtatcag aagtgttgca atctattcga gaaattcttc
2101 cctagcagtt cgtacaggag accagttgga atttccagca tggtggaggc catggtgtct
2161 agggcccgga ttgatgcacg gattgacttc gagtctggac ggattaagaa agaggagttc
2221 gctgagatca tgaagatctg ttccaccatt gaagagctca gacggcaaaa atag
```

SEQ ID NO: 7

MERIKELRNLMSQSRTREILTKTTVDHMAIIKKYTSGRQEKNPS

LRMKWMMAMKYPITADKRITEMIPERNEQGQTLWSKMSDAGSDRVMVSPLAVTW

WNRNGPMTSTVHYPKIYKTYFEKVERLKHGTFGPVHFRNQVKIRRRVDINPGHADL

SAKEAQDVIMEVVFPNEVGARILTSESQLTITKEKKEELQDCKISPLMVAYMLERELV

RKTRFLPVAGGTSSVYIEVLHLTQGTCWEQMYTPGGEVRNDDVDQSLIIAARNIVRR

AAVSADP

LASLLEMCHSTQIGGTRMVDILRQNPTEEQAVEICKAAMGLRISSSFSFGGFTFKRTS

GSSVKREEEVLTGNLQTLKIRVHEGYEEFTMVGKRATAILRKATRRLIQLIVSGRDEQ

SIAEAIIVAMVFSQEDCMIKAVRGDLNFVNRANQRLNPMHQLLRHFQKDAKVLFQN

WGIEHIDNVMGMIGVLPDMTPSTEMSMRGVRVSKMGVDEYSSAERVVVSIDRFLRV

RDQR

GNVLLSPEEVSETQGTEKLTITYSSSMMWEINGPESVLVNTYQWIIRNWETVKIQWS

QNPTMLYNKMEFEPFQSLVPKAIRGQYSGFVRTLFQQMRDVLGTFDTTQIIKLLPFA

AAPPKQSRMQFSSLTVNVRGSGMRILVRGNSPIFNYNKTTKRLTILGKDAGTLTEDP

DEGTSGVESAVLRGFLILGKEDRRYGPALSINELSNLAKGEKANVLIGQGDVVLVMK

RKRN

SSILTDSQTATKRIRMAIN

SEQ ID NO: 8

IKELWDLMSQSRTREILTKTTVDHMAIIKKYTSGRQEKNPALRM

KWMMAMKYPITADKRIMEMIPERNEQGQTLWSKTNDAGSDRVMESPLAVTWWNR

NGPTTSTVHYPKVYKTYFEKVERLKHGTFGPVHFRNQVKIRRRVDMNPGHADLSAK

EAQDVIMEVVFPNEVGARILTSESQLTITKEKREELKNCNIAPLMVAYMLERELVRKT

RFLPVA

GGTSSVYIEVLHLTQGTCWEQMYTPGGEVRNDDVDQSLIIAVGNIVRRATVSADPLA

SLLEMCHSTQIGGVRMVDILKQNPTEEQAVDICKAAMGLKISSSFSFGGFTFKRTKGS

SVKREEEVLTGNLQTLKIKVHEGYEEFTMVGRRATAILRKATRRMIQLIVSGRDEQSI

```
AEAIIVAMVFSQEDCMIKAVRGDLNFVNRANQRLNPMHQLLRHFQKDAKVLFQNW

GTEPIDNVMGMIGILPDMTPSTEMSLRGVRVSKMGVDEYSSTERVVVSIDRFLRVRD

QRGNVLLSPEEVSETQGMEKLTITYSSSMMWEINGPESVLVNTYQWIIRNWETVKIQ

WSQEPTMLYNKMEFEPFQSLVPKAARSQYSGFVRTLFQQMRDVLGTFDTVQIIKLLP

FAAAPPEQSRMQFSSLTVNVRGSGMRILVRGNSPAFNYNKTTKRLTILGKDAGALTE

DPDEGTAGVESAVLRGFLILGKEDKRYGPALSINELSNLTKGEKANVLIGQGDVVLV

MKRKRDSSI

LTDSQTATKRI
```

SEQ ID NO: 9

```
MERIKELRDLMSQSRTREILTKTTVDHMAIIKKYTSGRQEKNPA

LRMKWMMAMKYPITADKRIMEMIPERNEQGQTLWSKTNDAGSDRVMVSPLAVTW

WNRNGPTTSTVHYPKVYKTYFEKVERLKHGTFGPVHFRNQVKIRRRVDINPGHADL

SAKEAQDVIMEVVFPNEVGARILTSESQLTITKEKKKELQDCKIAPLMVAYMLEREL

VRKTRFL

PVAGGTSSVYIEVLHLTQGTCWEQMYTPGGEVRNDDVDQSLIIAARNIVRRATVSAD

PLASLLEMCHSTQIGGIRMVDILRQNPTEEQAVDICKAAMGLRISSSFSFGGFTFKRTS

GSSVKREEEVLTGNLQTLKIRVHEGYEEFTMVGRRATAILRKATRRLIQLIVSGKDEQ

SIAEAIIVAMVFSQEDCMIKAVRGDLNFVNRANQRLNPMHQLLRHFQKDAKVLFQN

WG

IEPIDNVMGMIGILPDMTPSTEMSLRGVRVSKMGVDEYSSTERVVVSIDRFLRVRDQ

RGNVLLSPEEVSETQGTEKLTITYSSSMMWEINGPESVLVNTYQWIIRNWENVKIQW

SQDPTMLYNKMEFEPFQSLVPKAARGQYSGFVRVLFQQMRDVLGTFDTVQIIKLLPF

AAAPPKQSRMQFSSLTVNVRGSGMRIVVRGNSPVFNYNKATKRLTVLGKDAGALM

EDPDEG

TAGVESAVLRGFLILGKEDKRYGPALSINELSNLAKGEKANVLIGQGDVVLVMKRK

RDSSILTDSQTATKRIRMAIN
```

SEQ ID NO: 10

```
SRTREILTKTTVDHMAIIKKYTSGRQEKNPSLRMKWMMAMKYPI

TADKRIMEMIPERNEQGQTLWSKTNDAGSNRVMVSPLAVTWWNRNGPTTSTIHYPK

VYKTYFEKVERLKHGTFGPVHFRNQVKIRRRVDVNPGHADLSAKEAQDVIMEVVFP

NEVGARILTSESQLAITKEKKEE
```

---

What is claimed is:

1. A modified influenza A virus comprising a PB1 polymerase, wherein the PB1 polymerase comprises a leucine to glutamine substitution (L319Q) at an amino acid corresponding to amino acid 319 of SEQ ID NO: 2.

2. The virus of claim 1, wherein the PB1 polymerase further comprises one or more mutations selected from the group consisting of a lysine to glutamic acid substitution at position 391 (K391E), a glutamic acid to glycine substitution at position 581 (E581G) and an alanine to threonine substitution at position 661 (A661T).

3. The virus of claim 1, wherein the virus further comprises a PB2 polymerase comprising an asparagine to serine substitution at position 265 (N265S).

4. The virus of claim 1, wherein the virus further comprises an influenza virus nucleoprotein (NP) comprising an aspartic acid to glycine substitution at position 35 (D35G).

5. The virus of claim 1, wherein the influenza A virus is selected from the group consisting of an H2N2 virus, an H3N2 virus, an H1N1 virus, an H9N2 virus and an H5N1 virus.

6. The virus of claim 1, wherein the influenza A virus is A/Ann Arbor/6/60 (H2N2).

7. The virus of claim 1, wherein the virus is a live attenuated influenza A virus with reduced growth from about 37° C. to about 39° C., as compared to an influenza A virus comprising a PB1 polymerase lacking a leucine to glutamine substitution (L319Q) at an amino acid corresponding to amino acid 319 of SEQ ID NO: 2.

8. An immunogenic composition comprising the virus of claim 1 and a pharmaceutically acceptable carrier.

9. A method for eliciting an immune response against an influenza A virus in a subject, comprising administering an effective dose of the immunogenic composition of claim 8 to the subject.

10. A method of producing an influenza A virus, comprising:
   a) transfecting a population of host cells with one or more vectors comprising
      i) nucleic acid sequences encoding the internal genome segments of an influenza A virus and;
      ii) a nucleic acid encoding a PB1 polymerase with a leucine to glutamine substitution (L319Q) at an amino acid corresponding to amino acid 319 of SEQ ID NO: 2;
   b) culturing the host cells; and
   c) recovering the modified influenza A virus.

11. The method of claim 10, wherein the nucleic acid encoding the PB1 polymerase further comprises one or more mutations selected from the group consisting of a lysine to glutamic acid substitution at position 391 (K391E), a glutamic acid to glycine substitution at position 581 (E581G) and an alanine to threonine substitution at position 661 (A661T).

12. The method of claim 10, further comprising transforming the cells with a nucleic acid encoding a PB2 polymerase comprising a N265S mutation.

13. The method of claim 10, further comprising transforming the cells with a nucleic acid encoding an NP protein comprising a D35G mutation.

14. The method of claim 10, wherein the influenza A virus is selected from the group consisting of an H2N2 virus, an H3N2 virus, an H1N1 virus, an H9N2 virus and an H5N1 virus.

15. The method of claim 10, wherein the cells are Vero cells, MDCK cells or CEK cells.

16. A method for producing an influenza A virus comprising:
   a) infecting a population of cells with the virus of claim 1;
   b) culturing the cells;
   c) harvesting the virus from the culture of step b).

17. The method of claim 16, wherein the cell is a mammalian cell or an avian cell.

18. A population of isolated cells comprising the virus of claim 1.

* * * * *

SEQUENCE LISTING

<160> NUMBER OF SEQ ID NOS: 10

<210> SEQ ID NO 1
<211> LENGTH: 16
<212> TYPE: PRT
<213> ORGANISM: Artificial sequence
<220> FEATURE:
<223> OTHER INFORMATION: Synthetic construct

<400> SEQUENCE: 1

Asn Glu Asn Gln Asn Pro Arg Met Phe Leu Ala Met Ile Thr Tyr Ile
1               5                   10                  15

<210> SEQ ID NO 2
<211> LENGTH: 757
<212> TYPE: PRT
<213> ORGANISM: Influenza A virus

<400> SEQUENCE: 2

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala His
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Lys Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380
```

Thr Arg Lys Lys Ile Glu Lys Ile Arg Pro Leu Leu Ile Asp Gly Thr
385                 390                 395                 400

Val Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
530                 535                 540

Gln Leu Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755

<210> SEQ ID NO 3
<211> LENGTH: 757
<212> TYPE: PRT
<213> ORGANISM: Influenza A virus

<400> SEQUENCE: 3

```
Met Asp Val Asn Pro Thr Leu Leu Phe Leu Lys Ile Pro Ala Gln Asn
1               5                   10                  15
Ala Ile Ser Thr Thr Phe Pro Tyr Thr Gly Asp Pro Pro Tyr Ser His
            20                  25                  30
Gly Thr Gly Thr Gly Tyr Thr Met Asp Thr Val Asn Arg Thr His Gln
        35                  40                  45
Tyr Ser Glu Lys Gly Lys Trp Thr Thr Asn Thr Glu Thr Gly Ala Pro
    50                  55                  60
Gln Leu Asn Pro Ile Asp Gly Pro Leu Pro Glu Asp Asn Glu Pro Ser
65                  70                  75                  80
Gly Tyr Ala Gln Thr Asp Cys Val Leu Glu Ala Met Ala Phe Leu Glu
                85                  90                  95
Glu Ser His Pro Gly Ile Phe Glu Asn Ser Cys Leu Glu Thr Met Glu
            100                 105                 110
Val Val Gln Gln Thr Arg Val Asp Lys Leu Thr Gln Gly Arg Gln Thr
        115                 120                 125
Tyr Asp Trp Thr Leu Asn Arg Asn Gln Pro Ala Ala Thr Ala Leu Ala
    130                 135                 140
Asn Thr Ile Glu Val Phe Arg Ser Asn Gly Leu Thr Ala Asn Glu Ser
145                 150                 155                 160
Gly Arg Leu Ile Asp Phe Leu Lys Asp Val Met Glu Ser Met Asn Lys
                165                 170                 175
Glu Glu Ile Glu Ile Thr Thr His Phe Gln Arg Lys Arg Arg Val Arg
            180                 185                 190
Asp Asn Met Thr Lys Lys Met Val Thr Gln Arg Thr Ile Gly Lys Lys
        195                 200                 205
Lys Gln Arg Leu Asn Lys Arg Gly Tyr Leu Ile Arg Ala Leu Thr Leu
    210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Ser Ile Cys Glu Lys Leu Glu Gln Ser Gly Leu Pro
            260                 265                 270
Val Gly Gly Asn Glu Lys Lys Ala Lys Leu Ala Asn Val Val Arg Lys
        275                 280                 285
Met Met Thr Asn Ser Gln Asp Thr Glu Ile Ser Phe Thr Ile Thr Gly
    290                 295                 300
Asp Asn Thr Lys Trp Asn Glu Asn Gln Asn Pro Arg Met Phe Leu Ala
305                 310                 315                 320
Met Ile Thr Tyr Ile Thr Arg Asn Gln Pro Glu Trp Phe Arg Asn Ile
                325                 330                 335
Leu Ser Met Ala Pro Ile Met Phe Ser Asn Lys Met Ala Arg Leu Gly
            340                 345                 350
Lys Gly Tyr Met Phe Glu Ser Lys Arg Met Lys Ile Arg Thr Gln Ile
        355                 360                 365
Pro Ala Glu Met Leu Ala Ser Ile Asp Leu Lys Tyr Phe Asn Glu Ser
    370                 375                 380
Thr Lys Lys Lys Ile Glu Lys Ile Arg Pro Leu Leu Ile Asp Gly Thr
385                 390                 395                 400
Ala Ser Leu Ser Pro Gly Met Met Met Gly Met Phe Asn Met Leu Ser
                405                 410                 415
```

```
Thr Val Leu Gly Val Ser Ile Leu Asn Leu Gly Gln Lys Lys Tyr Thr
            420                 425                 430

Lys Thr Ile Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
        450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
            485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
            565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Asp Tyr Arg Gly Arg Leu
610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
            645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Val Asp Phe Glu Ser Gly Arg Ile Lys
            725                 730                 735

Lys Glu Glu Phe Ser Glu Ile Met Lys Ile Cys Ser Thr Ile Glu Glu
            740                 745                 750

Leu Arg Arg Gln Lys
        755

<210> SEQ ID NO 4
<211> LENGTH: 757
<212> TYPE: PRT
<213> ORGANISM: Influenza A virus

<400> SEQUENCE: 4

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
```

```
                    20                  25                  30
Gly Thr Gly Thr Gly Tyr Thr Met Asp Thr Val Asn Arg Thr His Gln
                35                  40                  45
Tyr Ser Glu Arg Gly Lys Trp Thr Asn Thr Glu Thr Gly Ala Pro
 50                  55                  60
Gln Leu Asn Pro Ile Asp Gly Pro Leu Pro Glu Asp Asn Glu Pro Ser
 65                  70                  75                  80
Gly Tyr Ala Gln Thr Asp Cys Val Leu Glu Ala Met Ala Phe Leu Glu
                 85                  90                  95
Glu Ser His Pro Gly Ile Phe Glu Asn Ser Cys Leu Glu Thr Met Glu
                100                 105                 110
Ala Val Gln Gln Thr Arg Val Asp Lys Leu Thr Gln Gly Arg Gln Thr
                115                 120                 125
Tyr Asp Trp Thr Leu Asn Arg Asn Gln Pro Ala Ala Thr Ala Leu Ala
                130                 135                 140
Asn Thr Ile Glu Val Phe Arg Ser Asn Gly Leu Thr Ala Asn Glu Ser
145                 150                 155                 160
Gly Arg Leu Ile Asp Phe Leu Lys Asp Val Met Glu Ser Met Asp Lys
                165                 170                 175
Glu Glu Met Glu Ile Thr Thr His Phe Gln Arg Lys Arg Arg Val Arg
                180                 185                 190
Asp Asn Met Thr Lys Lys Met Val Thr Gln Arg Thr Ile Gly Lys Lys
                195                 200                 205
Lys Gln Arg Val Asn Lys Arg Gly Tyr Leu Ile Arg Ala Leu Thr Leu
                210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Ser Ile Cys Glu Lys Leu Glu Gln Ser Gly Leu Pro
                260                 265                 270
Val Gly Gly Asn Glu Lys Lys Ala Lys Leu Ala Asn Val Val Arg Lys
                275                 280                 285
Met Met Thr Asn Ser Gln Asp Thr Glu Leu Ser Phe Thr Ile Thr Gly
                290                 295                 300
Asp Asn Thr Lys Trp Asn Glu Asn Gln Asn Pro Arg Met Phe Leu Ala
305                 310                 315                 320
Met Ile Thr Tyr Ile Thr Lys Asn Gln Pro Glu Trp Phe Arg Asn Ile
                325                 330                 335
Leu Ser Ile Ala Pro Ile Met Phe Ser Asn Lys Met Ala Arg Leu Gly
                340                 345                 350
Lys Gly Tyr Met Phe Glu Ser Lys Lys Met Lys Leu Arg Thr Gln Ile
                355                 360                 365
Pro Ala Glu Met Leu Ala Ser Ile Asp Leu Lys Tyr Phe Asn Glu Ser
                370                 375                 380
Thr Arg Lys Lys Ile Glu Lys Ile Arg Pro Leu Leu Ile Asp Gly Thr
385                 390                 395                 400
Ala Ser Leu Ser Pro Gly Met Met Met Gly Met Phe Asn Met Leu Ser
                405                 410                 415
Thr Val Leu Gly Val Ser Ile Leu Asn Leu Gly Gln Lys Lys Tyr Thr
                420                 425                 430
Lys Thr Thr Tyr Trp Trp Asp Gly Leu Gln Ser Ser Asp Asp Phe Ala
                435                 440                 445
```

-continued

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Asp Gln Thr Gln Ser Arg Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asn Tyr Arg Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Arg Ile Cys Ser Thr Ile Glu Glu
            740                 745                 750

Leu Arg Arg Gln Lys
        755

<210> SEQ ID NO 5
<211> LENGTH: 744
<212> TYPE: PRT
<213> ORGANISM: Influenza A virus

<400> SEQUENCE: 5

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro

```
                50              55              60
        Gln Leu Asn Pro Ile Asp Gly Pro Leu Pro Glu Asp Asn Glu Pro Ser
        65                  70                  75                  80

Gly Tyr Ala Gln Thr Asp Cys Val Leu Glu Ala Met Ala Phe Leu Glu
                        85                  90                  95

Glu Ser His Pro Gly Leu Phe Glu Asn Ser Cys Leu Glu Thr Met Glu
                    100                 105                 110

Val Val Gln Gln Thr Arg Val Asp Lys Leu Thr Gln Gly Arg Gln Thr
                115                 120                 125

Tyr Asp Trp Thr Leu Asn Arg Asn Gln Pro Ala Ala Thr Ala Leu Ala
            130                 135                 140

Asn Thr Ile Glu Val Phe Arg Ser Asn Gly Leu Thr Ala Asn Glu Ser
        145                 150                 155                 160

Gly Arg Leu Ile Asp Phe Leu Lys Asp Val Met Glu Ser Met Asp Lys
                        165                 170                 175

Glu Glu Met Glu Ile Thr Thr His Phe Gln Arg Lys Arg Arg Val Arg
                    180                 185                 190

Asp Asn Met Thr Lys Lys Met Val Thr Gln Arg Thr Ile Gly Lys Lys
                195                 200                 205

Lys Gln Lys Leu Thr Lys Lys Ser Tyr Leu Ile Arg Ala Leu Thr Leu
            210                 215                 220

Asn Thr Met Thr Lys Asp Ala Glu Arg Gly Lys Leu Lys Arg Arg Ala
        225                 230                 235                 240

Ile Ala Thr Pro Gly Met Gln Ile Arg Gly Phe Val His Phe Val Glu
                        245                 250                 255

Ala Leu Ala Arg Ser Ile Cys Glu Lys Leu Glu Gln Ser Gly Leu Pro
                    260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Val Thr Gly
            290                 295                 300

Asp Asn Thr Lys Trp Asn Glu Asn Gln Asn Pro Arg Ile Phe Leu Ala
        305                 310                 315                 320

Met Ile Thr Tyr Ile Thr Arg Asn Gln Pro Glu Trp Phe Arg Asn Val
                        325                 330                 335

Leu Ser Ile Ala Pro Ile Met Phe Ser Asn Lys Met Ala Arg Leu Gly
                    340                 345                 350

Lys Gly Tyr Met Phe Glu Ser Lys Ser Met Lys Leu Arg Thr Gln Ile
                355                 360                 365

Pro Ala Glu Met Leu Ala Asn Ile Asp Leu Lys Tyr Phe Asn Glu Ser
            370                 375                 380

Thr Arg Lys Lys Ile Glu Lys Ile Arg Pro Leu Leu Ile Glu Gly Thr
        385                 390                 395                 400

Ala Ser Leu Ser Pro Gly Met Met Met Gly Met Phe Asn Met Leu Ser
                        405                 410                 415

Thr Val Leu Gly Val Ser Ile Leu Asn Leu Gly Gln Lys Arg Tyr Thr
                    420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Ile Gln Ala Gly Val Asp
            450                 455                 460

Arg Phe Tyr Arg Thr Cys Lys Leu Val Gly Ile Asn Met Ser Lys Lys
        465                 470                 475                 480
```

```
Lys Ser Tyr Ile Asn Arg Thr Gly Thr Phe Glu Phe Thr Ser Phe
                485                 490                 495
Tyr Arg Tyr Gly Phe Val Ala Asn Phe Ser Met Glu Leu Pro Ser Phe
            500                 505                 510
Gly Val Ser Gly Ile Asn Glu Ser Ala Asp Met Ser Ile Gly Val Thr
            515                 520                 525
Val Ile Lys Asn Asn Met Ile Asn Asn Asp Leu Gly Pro Ala Thr Ala
    530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Leu
                565                 570                 575
Lys Lys Leu Trp Glu Gln Thr Arg Ser Lys Ala Gly Leu Leu Val Ser
            580                 585                 590
Asp Gly Gly Pro Asn Leu Tyr Asn Ile Arg Asn Leu His Ile Pro Glu
            595                 600                 605
Val Gly Leu Lys Trp Glu Leu Met Asp Glu Asp Tyr Gln Gly Arg Leu
    610                 615                 620
Cys Asn Pro Leu Asn Pro Phe Val Ser His Lys Glu Val Glu Ser Val
625                 630                 635                 640
Asn Asn Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Ile Leu Glu Asp Glu Gln Met
            675                 680                 685
Tyr Gln Lys Cys Cys Thr Leu Phe Glu Lys Phe Phe Pro Ser Ser Ser
    690                 695                 700
Tyr Arg Arg Pro Val Gly Ile Ser Ser Met Met Glu Ala Met Val Ser
705                 710                 715                 720
Arg Ala Arg Ile Asp Ala Arg Ile Asp Phe Glu Ser Gly Arg Ile Lys
                725                 730                 735
Lys Glu Glu Phe Ala Glu Ile Leu
            740

<210> SEQ ID NO 6
<211> LENGTH: 2274
<212> TYPE: DNA
<213> ORGANISM: Influenza A virus

<400> SEQUENCE: 6
atggatgtca atccgacctt acttttcttg aaagttccag cgcaaaatgc cataagtact      60
acattcccct tatactggag tcctccatac agccatggaa caggaacagg atacaccatg     120
gacacagtca acagaacaca tcaatattca gaaaggggga agtggacaac aaacacggaa     180
actggagcgc accaacttaa cccaattgat ggaccactac ctgaggacaa tgaaccaagt     240
ggatatgcac aaacagactg cgtcctggaa gcaatggctt tccttgaaga tcccacccca     300
ggaatctttg aaaactcgtg tcttgaaacg atggaagtta ttcaacaaac aagagtggac     360
aaactgaccc aaggtcgtca gacctatgat tggacattga acagaaatca gccggctgca     420
actgcgctag ccaacactat agaggtcttc agatcgaatg gcctgacagc taatgaatcg     480
ggaaggctaa tagatttcct caaggatgtg atagaatcaa tggataaaga ggagatggaa     540
atcacaacac acttccaaag aaaaagaaga gtaagagaca catgaccaa gaaaatggtc     600
```

```
acacaacgaa caataggaaa gaagaagcaa agattgaaca agagaagcta tctaataaga    660
gcactgacat tgaacacaat gactaaagat gcagagagag gtaaattaaa gagaagagca    720
attgcaacac ccggtatgca gatcagaggg ttcgtgtact tgtcgaaac actagcgaga     780
agtatttgtg agaagcttga acagtctggg cttccggttg gaggtaatga aaagaaggct    840
aaactggcaa atgttgtgcg aaaaatgatg actaattcac aagacacaga gctctctttc    900
acaattactg gagacaatac caaatggaat gagaatcaaa atcctcggat gttcctggcg    960
atgataacat acatcacaag aaatcaacct gaatggttta gaaacgtcct gagcatcgca   1020
cctataatgt tctcaaataa aatggcaaga ctagggaaag gatacatgtt caaaagcaag   1080
agcatgaagc tccgaacaca ataccagca gaaatgctag caagtattga cctgaaatac    1140
tttaatgaat caacaagaaa gaaaatcgag aaaataaggc ctctcctaat agatggcaca   1200
gtctcattga gtcctggaat gatgatgggc atgttcaaca tgctaagtac agtcttagga   1260
gtctcaatcc tgaatcttgg acaaaagaag tacaccaaaa caacatactg gtgggacgga   1320
ctccaatcct ctgatgactt cgccctcata gtgaatgcac caaatcatga gggaatacaa   1380
gcaggggtgg atagattcta cagaacctgc aagctagtcg aatcaatat gagcaaaaag    1440
aagtcctaca taaataggac agggacattt gaattcacaa gcttttttcta tcgctatgga  1500
tttgtagcca attttagcat ggagctgccc agctttggag tgtctggaat taatgaatcg   1560
gctgatatga gcattggggt aacagtgata aagaacaaca tgataaacaa tgaccttggg   1620
ccagcaacag cccaactggc tcttcaacta ttcatcaaag actacagata tacgtaccgg   1680
tgccacagag gagacacaca aattcagaca aggagatcat tcgagctaaa gaagctgtgg   1740
gagcaaaccc gctcaaaggc aggacttttg gtttcggatg gaggaccaaa cttatacaat   1800
atccggaatc tccacattcc agaagtctgc ttgaagtggg agctaatgga tgaagactat   1860
caggggaggc tttgtaatcc cctgaatcca tttgtcagtc ataaggagat tgagtctgta   1920
aacaatgctg tggtaatgcc agctcacggt ccagccaaga gcatggaata tgatgctgtt   1980
gctactacac actcctggat ccctaagagg aaccgctcca ttctcaacac aagccaaagg   2040
ggaattcttg aagatgaaca gatgtatcag aagtgttgca atctattcga gaaattcttc   2100
cctagcagtt cgtacaggag accagttgga atttccagca tggtggaggc catggtgtct   2160
agggcccgga ttgatgcacg gattgacttc gagtctggac ggattaagaa agaggagttc   2220
gctgagatca tgaagatctg ttccaccatt gaagagctca gacggcaaaa atag           2274
```

<210> SEQ ID NO 7
<211> LENGTH: 759
<212> TYPE: PRT
<213> ORGANISM: Influenza A virus

<400> SEQUENCE: 7

```
Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80
```

```
Met Ser Asp Ala Gly Ser Asp Arg Val Met Val Ser Pro Leu Ala Val
                85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Glu Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Asn Val Met Gly Met Ile Gly Val Leu
    450                 455                 460

Pro Asp Met Thr Pro Ser Thr Glu Met Ser Met Arg Gly Val Arg Val
465                 470                 475                 480

Ser Lys Met Gly Val Asp Glu Tyr Ser Ser Ala Glu Arg Val Val Val
                485                 490                 495
```

```
Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
        610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Ile Phe
                645                 650                 655

Asn Tyr Asn Lys Thr Thr Lys Arg Leu Thr Ile Leu Gly Lys Asp Ala
            660                 665                 670

Gly Thr Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Arg Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asn Ser Ser Ile Leu Thr Asp Ser Gln Thr Ala Thr Lys
            740                 745                 750

Arg Ile Arg Met Ala Ile Asn
            755

<210> SEQ ID NO 8
<211> LENGTH: 751
<212> TYPE: PRT
<213> ORGANISM: Influenza A virus

<400> SEQUENCE: 8

Ile Lys Glu Leu Trp Asp Leu Met Ser Gln Ser Arg Thr Arg Glu Ile
1               5                   10                  15

Leu Thr Lys Thr Thr Val Asp His Met Ala Ile Ile Lys Lys Tyr Thr
            20                  25                  30

Ser Gly Arg Gln Glu Lys Asn Pro Ala Leu Arg Met Lys Trp Met Met
        35                  40                  45

Ala Met Lys Tyr Pro Ile Thr Ala Asp Lys Arg Ile Met Glu Met Ile
    50                  55                  60

Pro Glu Arg Asn Glu Gln Gly Gln Thr Leu Trp Ser Lys Thr Asn Asp
65                  70                  75                  80

Ala Gly Ser Asp Arg Val Met Glu Ser Pro Leu Ala Val Thr Trp Trp
                85                  90                  95

Asn Arg Asn Gly Pro Thr Thr Ser Thr Val His Tyr Pro Lys Val Tyr
            100                 105                 110
```

-continued

```
Lys Thr Tyr Phe Glu Lys Val Glu Arg Leu Lys His Gly Thr Phe Gly
            115                 120                 125

Pro Val His Phe Arg Asn Gln Val Lys Ile Arg Arg Arg Val Asp Met
        130                 135                 140

Asn Pro Gly His Ala Asp Leu Ser Ala Lys Glu Ala Gln Asp Val Ile
145                 150                 155                 160

Met Glu Val Val Phe Pro Asn Glu Val Gly Ala Arg Ile Leu Thr Ser
                165                 170                 175

Glu Ser Gln Leu Thr Ile Thr Lys Glu Lys Arg Glu Glu Leu Lys Asn
                180                 185                 190

Cys Asn Ile Ala Pro Leu Met Val Ala Tyr Met Leu Glu Arg Glu Leu
                195                 200                 205

Val Arg Lys Thr Arg Phe Leu Pro Val Ala Gly Gly Thr Ser Ser Val
        210                 215                 220

Tyr Ile Glu Val Leu His Leu Thr Gln Gly Thr Cys Trp Glu Gln Met
225                 230                 235                 240

Tyr Thr Pro Gly Gly Glu Val Arg Asn Asp Asp Val Asp Gln Ser Leu
                245                 250                 255

Ile Ile Ala Val Gly Asn Ile Val Arg Arg Ala Thr Val Ser Ala Asp
                260                 265                 270

Pro Leu Ala Ser Leu Leu Glu Met Cys His Ser Thr Gln Ile Gly Gly
        275                 280                 285

Val Arg Met Val Asp Ile Leu Lys Gln Asn Pro Thr Glu Glu Gln Ala
        290                 295                 300

Val Asp Ile Cys Lys Ala Ala Met Gly Leu Lys Ile Ser Ser Ser Phe
305                 310                 315                 320

Ser Phe Gly Gly Phe Thr Phe Lys Arg Thr Lys Gly Ser Ser Val Lys
                325                 330                 335

Arg Glu Glu Glu Val Leu Thr Gly Asn Leu Gln Thr Leu Lys Ile Lys
                340                 345                 350

Val His Glu Gly Tyr Glu Glu Phe Thr Met Val Gly Arg Arg Ala Thr
        355                 360                 365

Ala Ile Leu Arg Lys Ala Thr Arg Arg Met Ile Gln Leu Ile Val Ser
        370                 375                 380

Gly Arg Asp Glu Gln Ser Ile Ala Glu Ala Ile Ile Val Ala Met Val
385                 390                 395                 400

Phe Ser Gln Glu Asp Cys Met Ile Lys Ala Val Arg Gly Asp Leu Asn
                405                 410                 415

Phe Val Asn Arg Ala Asn Gln Arg Leu Asn Pro Met His Gln Leu Leu
                420                 425                 430

Arg His Phe Gln Lys Asp Ala Lys Val Leu Phe Gln Asn Trp Gly Thr
        435                 440                 445

Glu Pro Ile Asp Asn Val Met Gly Met Ile Gly Ile Leu Pro Asp Met
        450                 455                 460

Thr Pro Ser Thr Glu Met Ser Leu Arg Gly Val Arg Val Ser Lys Met
465                 470                 475                 480

Gly Val Asp Glu Tyr Ser Ser Thr Glu Arg Val Val Val Ser Ile Asp
                485                 490                 495

Arg Phe Leu Arg Val Arg Asp Gln Arg Gly Asn Val Leu Leu Ser Pro
                500                 505                 510

Glu Glu Val Ser Glu Thr Gln Gly Met Glu Lys Leu Thr Ile Thr Tyr
        515                 520                 525
```

-continued

Ser Ser Ser Met Met Trp Glu Ile Asn Gly Pro Glu Ser Val Leu Val
            530                 535                 540

Asn Thr Tyr Gln Trp Ile Ile Arg Asn Trp Glu Thr Val Lys Ile Gln
545                 550                 555                 560

Trp Ser Gln Glu Pro Thr Met Leu Tyr Asn Lys Met Glu Phe Glu Pro
                565                 570                 575

Phe Gln Ser Leu Val Pro Lys Ala Ala Arg Ser Gln Tyr Ser Gly Phe
            580                 585                 590

Val Arg Thr Leu Phe Gln Gln Met Arg Asp Val Leu Gly Thr Phe Asp
        595                 600                 605

Thr Val Gln Ile Ile Lys Leu Leu Pro Phe Ala Ala Pro Pro Glu
    610                 615                 620

Gln Ser Arg Met Gln Phe Ser Ser Leu Thr Val Asn Val Arg Gly Ser
625                 630                 635                 640

Gly Met Arg Ile Leu Val Arg Gly Asn Ser Pro Ala Phe Asn Tyr Asn
                645                 650                 655

Lys Thr Thr Lys Arg Leu Thr Ile Leu Gly Lys Asp Ala Gly Ala Leu
                660                 665                 670

Thr Glu Asp Pro Asp Glu Gly Thr Ala Gly Val Glu Ser Ala Val Leu
        675                 680                 685

Arg Gly Phe Leu Ile Leu Gly Lys Glu Asp Lys Arg Tyr Gly Pro Ala
690                 695                 700

Leu Ser Ile Asn Glu Leu Ser Asn Leu Thr Lys Gly Glu Lys Ala Asn
705                 710                 715                 720

Val Leu Ile Gly Gln Gly Asp Val Val Leu Val Met Lys Arg Lys Arg
                725                 730                 735

Asp Ser Ser Ile Leu Thr Asp Ser Gln Thr Ala Thr Lys Arg Ile
            740                 745                 750

<210> SEQ ID NO 9
<211> LENGTH: 759
<212> TYPE: PRT
<213> ORGANISM: Influenza A virus

<400> SEQUENCE: 9

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Met
    50                  55                  60

Glu Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
                100                 105                 110

Lys Val Tyr Lys Thr Tyr Phe Glu Lys Val Glu Arg Leu Lys His Gly
            115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

-continued

```
Asp Val Ile Met Glu Val Val Phe Pro Asn Glu Val Gly Ala Arg Ile
            165                 170                 175
Leu Thr Ser Glu Ser Gln Leu Thr Ile Thr Lys Glu Lys Lys Lys Glu
            180                 185                 190
Leu Gln Asp Cys Lys Ile Ala Pro Leu Met Val Ala Tyr Met Leu Glu
            195                 200                 205
Arg Glu Leu Val Arg Lys Thr Arg Phe Leu Pro Val Ala Gly Gly Thr
    210                 215                 220
Ser Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Val Asp
                245                 250                 255
Gln Ser Leu Ile Ile Ala Ala Arg Asn Ile Val Arg Arg Ala Thr Val
            260                 265                 270
Ser Ala Asp Pro Leu Ala Ser Leu Leu Glu Met Cys His Ser Thr Gln
    275                 280                 285
Ile Gly Gly Ile Arg Met Val Asp Ile Leu Arg Gln Asn Pro Thr Glu
    290                 295                 300
Glu Gln Ala Val Asp Ile Cys Lys Ala Ala Met Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Arg Glu Glu Val Leu Thr Gly Asn Leu Gln Thr Leu
            340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Arg Leu Ile Gln Leu
    370                 375                 380
Ile Val Ser Gly Lys Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Lys Val Leu Phe Gln Asn
    435                 440                 445
Trp Gly Ile Glu Pro Ile Asp Asn Val Met Gly Met Ile Gly Ile Leu
    450                 455                 460
Pro Asp Met Thr Pro Ser Thr Glu Met Ser Leu Arg Gly Val Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Val Leu
            500                 505                 510
Leu Ser Pro Glu Glu Val Ser Glu Thr Gln Gly Thr Glu Lys Leu Thr
    515                 520                 525
Ile Thr Tyr Ser Ser Ser Met Met Trp Glu Ile Asn Gly Pro Glu Ser
    530                 535                 540
Val Leu Val Asn Thr Tyr Gln Trp Ile Ile Arg Asn Trp Glu Asn Val
545                 550                 555                 560
Lys Ile Gln Trp Ser Gln Asp Pro Thr Met Leu Tyr Asn Lys Met Glu
                565                 570                 575
```

```
Phe Glu Pro Phe Gln Ser Leu Val Pro Lys Ala Ala Arg Gly Gln Tyr
                580                 585                 590

Ser Gly Phe Val Arg Val Leu Phe Gln Gln Met Arg Asp Val Leu Gly
            595                 600                 605

Thr Phe Asp Thr Val Gln Ile Ile Lys Leu Leu Pro Phe Ala Ala Ala
        610                 615                 620

Pro Pro Lys Gln Ser Arg Met Gln Phe Ser Ser Leu Thr Val Asn Val
625                 630                 635                 640

Arg Gly Ser Gly Met Arg Ile Val Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Met Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 10
<211> LENGTH: 179
<212> TYPE: PRT
<213> ORGANISM: Influenza A virus

<400> SEQUENCE: 10

Ser Arg Thr Arg Glu Ile Leu Thr Lys Thr Thr Val Asp His Met Ala
1               5                   10                  15

Ile Ile Lys Lys Tyr Thr Ser Gly Arg Gln Glu Lys Asn Pro Ser Leu
                20                  25                  30

Arg Met Lys Trp Met Met Ala Met Lys Tyr Pro Ile Thr Ala Asp Lys
            35                  40                  45

Arg Ile Met Glu Met Ile Pro Glu Arg Asn Glu Gln Gly Gln Thr Leu
        50                  55                  60

Trp Ser Lys Thr Asn Asp Ala Gly Ser Asn Arg Val Met Val Ser Pro
65                  70                  75                  80

Leu Ala Val Thr Trp Trp Asn Arg Asn Gly Pro Thr Thr Ser Thr Ile
                85                  90                  95

His Tyr Pro Lys Val Tyr Lys Thr Tyr Phe Glu Lys Val Glu Arg Leu
            100                 105                 110

Lys His Gly Thr Phe Gly Pro Val His Phe Arg Asn Gln Val Lys Ile
        115                 120                 125

Arg Arg Arg Val Asp Val Asn Pro Gly His Ala Asp Leu Ser Ala Lys
130                 135                 140

Glu Ala Gln Asp Val Ile Met Glu Val Val Phe Pro Asn Glu Val Gly
145                 150                 155                 160

Ala Arg Ile Leu Thr Ser Glu Ser Gln Leu Ala Ile Thr Lys Glu Lys
                165                 170                 175

Lys Glu Glu
```